(12) United States Patent
Druzgala et al.

(10) Patent No.: US 6,683,195 B2
(45) Date of Patent: *Jan. 27, 2004

(54) ENANTIOMERIC COMPOUNDS FOR TREATMENT OF CARDIAC ARRHYTHMIAS AND METHODS OF USE

(75) Inventors: Pascal Druzgala, Santa Rosa, CA (US); Peter G. Milner, Los Altos Hills, CA (US)

(73) Assignee: ARYx Therapeutics, Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/123,573

(22) Filed: Apr. 15, 2002

(65) Prior Publication Data

US 2002/0193428 A1 Dec. 19, 2002

Related U.S. Application Data

(63) Continuation-in-part of application No. PCT/US00/28636, filed on Oct. 13, 2000.
(60) Provisional application No. 60/159,609, filed on Oct. 15, 1999, and provisional application No. 60/290,089, filed on May 10, 2001.

(51) Int. Cl.$^7$ ............................................. C07D 307/78
(52) U.S. Cl. ....................................... 549/467; 549/468
(58) Field of Search .................................. 549/467, 468

(56) References Cited

U.S. PATENT DOCUMENTS

| | | | |
|---|---|---|---|
| 4,931,464 A | 6/1990 | Grover et al. | |
| 4,962,095 A | 10/1990 | Grover et al. | |
| 5,175,187 A | 12/1992 | Baligadoo | |
| 5,364,880 A | 11/1994 | Druzgala | |
| 5,440,054 A | 8/1995 | Druzgala | |
| 5,849,788 A | 12/1998 | Druzgala | |
| 6,362,223 B1 | 3/2002 | Druzgala et al. | |
| 6,372,783 B1 | 4/2002 | Druzgala et al. | |

FOREIGN PATENT DOCUMENTS

WO    WO 94/29289 A    12/1994

OTHER PUBLICATIONS

Cairns, John A., Stuart J. Connolly, Robin Roberts et al. (Mar. 8, 1997) "Randomised trial of outcome after myocardial infarction in patients with frequent or repetitive ventricular premature depolarisations: CAMIAT" *Lancet* 349:675–682.

Charlier et al. (1969) *Cardiologia* 54:82.

Connolly, S., J. Cairins, M. Gent et al. (Nov. 15, 1997) "Effect of prophylactic amiodarone on mortality after acute myocardial infarction and in congestive heart failure: meta–analysis of individual data from 6500 patients in randomised trials" *Lancet* 350:1417–1424.

Juhasz, A., N. Bodor (2000) "Cardiovascular Studies on Different Classes of Soft Drugs" *Pharmzie* 55(3):228–238.

Julian, D.G., A.J. Camm, G. Frangin et al. (Mar. 8, 1997) "Randomised trial of effect of amiodarone on mortality in patients with left–ventricular dysfunction after recent myocardial infarction: EMIAT" *Lancet*:349:667–674.

Kerr, Charles R. Mauricio B. Osenbaum, Pablo A. Chiale (1996) "Amiodarone" In: Cardiovascular Drug Therapy, Editor: Messerli, F.H.W.B. Saunders Co., 2$^{nd}$ Edition, Chapter 138, pp. 1247–1264.

Kowey, Peter R., Joseph H. Levine, John M. Herre et al. (Dec. 1, 1995) "Randomized, Double–Blind Comparison of Intravenous Amiodarone and Bretylium in the Treatment of Patients with Recurrent, Hemodynamically Destabilizing Ventricular Tachycardia or Fibrillation" *Circulation* 92(11)3255–3263.

Naccarelli, Gerald, Robert L. Rinkenberger, Anne H. Dougherty, Ruth A. Giebel (Nov./Dec. 1985) "Evaluations of New Drugs" *Pharmacotherapy* 5(6):298–313.

Rosenbaum, Mauricio B., Pablo A. Chiale, M. susana Halpern et al. (Dec. 1976) "Clinical Efficacy of Amiodarone as an Antiarrhythmic Agent" *The American Journal of Cardiology* 38:934–944.

Rosenabaum, Mauricio, Pablo A. chiale, David Ryba, Marcelo V. elizari (Aug. 1974) "Control of Tachyarrhythmias Associated with Wolff–Parkinson–White Syndrome by Amiodarone Hydrochloride" *The American Journal of Cardiology* 34:215–223.

Singh, B.N. and E.M. Vaughan Williams (1970) "The effect of amiodarone, a new anti–anginal drug, on cardiac muscle" *Br. J. Pharmacol* 39:657–667.

Vrobel, Thomas R., Paul E. Miller, Nelson D. Mostow, Louis Rakita (May/Jun. 1989) "A General Overview of Amiodarone Toxicity: Its Prevention, Detection, and Management" *Progress in Cardiovascular Diseases* 31(6):393–426.

*Primary Examiner*—Amelia Owens
(74) *Attorney, Agent, or Firm*—Saliwanchik, Lloyd & Saliwanchik

(57) ABSTRACT

The subject invention pertains to novel enantiomerically pure compounds, and compositions comprising the compounds, for the treatment of cardiac arrhythmias. The subject invention further concerns a method of making and purifying the compounds. The enantiomerically purified compounds, and compositions of these compounds, exhibit unexpectedly distinct and advantageous characteristics, such as a markedly superior ability to reduce or inhibit ventricular premature beats, as compared to racemic mixtures of the compounds.

40 Claims, 16 Drawing Sheets

ENANTIOMERIC COMPOUNDS FOR TREATMENT OF CARDIAC ARRHYTHMIAS AND METHODS OF USE

CROSS-REFERENCE TO A RELATED APPLICATION

This application is a continuation-in-part of PCT/US00/28636, filed Oct. 13, 2000, which claims priority to U.S. Ser. No. 09/680,873, filed Oct. 6, 2000, now U.S. Pat. No. 6,372,783, and Ser. No. 09/684,046, filed Oct. 6, 2000, now U.S. Pat. No. 6,362,223, both of which claim the benefit of provisional application serial No. 60/159,609, filed Oct. 15, 1999. This application also claims the benefit of U.S. Provisional Application No. 60/290,089, filed May 10, 2001.

BACKGROUND OF THE INVENTION

Congestive heart failure (CHF) is a disease affecting approximately 2% of the population of the United States (Sami, M. H. [1991] *J. Clin. Pharmacol.* 31:1081). Despite advances in the diagnosis and treatment of CHF, the prognosis remains poor with a 5-year mortality rate higher than 50% from the time of diagnosis (McFate Smith, W. [1985] *Am. J. Cardiol.* 55:3A; McKee, P. A., W. P. Castelli, P. M. McNamara, W. B. Kannel [1971] *N. Engl. J. Med.* 285:1441). In patients with CHF, the rate of survival is lowest in those patients with severe depression of left ventricular function and patients who have frequent ventricular arrhythmias. Patients with ventricular arrhythmias and ischemic cardiomyopathy have an increased risk of sudden death. The presence of ventricular tachycardia in patients with severe CHF results in a three-fold increase in sudden death compared to those without tachycardia (Bigger, J. T., Jr. [1987] *Circulation* 75(suppl.IV):28). Because of the high prevalence of sudden unexpected death in patients with CHF, there has been a growing interest in the prognostic significance of arrhythmias in these patients.

Several compounds have been used in the management of cardiac arrhythmias in patients with congestive heart failure. Unfortunately, anti-arrhythmic drug therapy has been disappointing. The efficacy of anti-arrhythmic drugs markedly decreases as left ventricular function declines, such that only a small fraction of patients with CHF are responsive to anti-arrhythmic therapy. No anti-arrhythmic drug has prevented sudden death in patients with CHF and there is even a question of increased mortality associated with certain anti-arrhythmic drugs (the CAST investigators [1989] *N. Engl. J. Med.* 321:406).

Scientists define tachycardia and ventricular fibrillation as being of multiple nature. It now seems clear, and is accepted in the art, that re-entry is the underlying mechanism to most sustained arrhythmias. Prolonging ventricular repolarization as a means of preventing ventricular arrhythmias has consequently received renewed attention. This points to Class-III agents as drugs of choice in the treatment of arrhythmias. A Class-III agent, as referred to herein, is an agent which is classified as such in the Vaughan-Williams classification of anti-arrhythmic drugs. A Class-III agent exerts its primary anti-arrhythmic activity by prolonging cardiac action potential duration (APD), and thereby the effective refractory period (ERP), with no effect on conduction. These electrophysiological changes, which are brought about by blockade of cardiac potassium channels, are well known in the art. Because the blockade of cardiac potassium channels is not associated with depression of the contractile function of the heart, Class-III agents are particularly attractive for use in patients with CHF. Unfortunately, the existing Class-III agents are limited in their utility by additional pharmacological activities, lack of good oral bioavailability, or a poor toxicity profile. Two Class III agents currently marketed are bretylium (i.v. only) and amiodarone (i.v. and p.o.).

Amiodarone is an anti-arrhythmic agent with complex electrophysiological activity including Class-I (sodium channel), Class-II (beta-receptor), Class-III (potassium channel), and even Class-IV (calcium channel) properties, thus acting on both cardiac conduction and cardiac repolarization parameters (Charlier et al., [1969] *Cardiologia,* 54:82; Singh et al., [1970] *Br. J. Pharmacol.* 39:657; Rosenbaum et al., [1974] *Am. J. Cardiol.* 34:215; Rosenbaum et al., [1976] *Am. J. Cardiol.* 38:934). The corresponding EKG effects are reduction in heart rate (HR) and prolongation of the PR, QRS and QT intervals (Naccarelli et al., [1985] *Pharmacotherapy,* 6:298). Because of these combined electrophysiological properties, amiodarone is effective against ventricular and supra-ventricular arrhythmias, including atrial fibrillation and flutter, paroxysmal supraventricular tachycardia, ventricular premature beats (VPB), sustained and non-sustained ventricular tachycardia (VT), and ventricular fibrillation (VF) (Naccarelli et al., [1985] *Pharmacotherapy,* 6:298; Kerr et al., [1996], In *Cardiovascular Drug Therapy,* $2^{nd}$ ed., Editor: Messerli, F. H. W. B. Saunders Co. pp. 1247–1264).

Amiodarone is one of the very few drugs that actually reduce mortality rates in high-risk patients (post-myocardial infarction patients and patients with congestive heart failure) (Cairns et al., [1997] *Lancet,* 349:675; Julian et al., [1997] *Lancet,* 349:667; Amiodarone Trials Meta-Analysis Investigators: Effect of Prophylactic Amiodarone on Mortality After Acute Myocardial Infarction and in Congestive Heart Failure: Meta-Analysis of Individual Data from 6500 Patients in Randomised Trials. *Lancet,* 1997, 350, 1417–24). Unfortunately, because of its life-threatening side-effects and the substantial management difficulties associated with its use, amiodarone is indicated only for life-threatening recurrent ventricular arrhythmias when these have not responded to documented adequate doses of other available anti-arrhythmics or when alternative agents are not tolerated (Vrobel et al., [1989] *Progr. In Cardiovasc. Dis.,* 31:393). The pharmacokinetic properties of amiodarone are characterized by slow absorption, moderate bioavailability, high lipophilicity, and a very large volume of distribution (60 L/kg on average). Its elimination is almost exclusively hepatic and its clearance rate is very slow. Its terminal elimination half-life is 53 days (Naccarelli et al., [1985] *Pharmacotherapy,* 6:298). As a consequence, upon long-term administration, amiodarone accumulates in virtually every organ including poorly perfused tissues such as the lens. The onset of its anti-arrhythmic activity may take days, or even weeks to appear. The onset of activity can be shortened with the administration of intravenous loading doses, but is still too long (Kowey et al., [1995] *Circulation,* 92:3255). Cardioprotective agents and methods which employ amiodarone in synergistic combination with vasodilators and beta blockers have been described for use in patients with coronary insufficiency (U.S. Pat. No. 5,175,187). Amiodarone has also been described for reducing arrhythmias associated with CHF as used in combination with anti-hypertensive agents, e.g., (S)-1-[6-amino-2-[[hydroxy(4-phenylbutyl)phosphinyl]oxyl]-L-proline (U.S. Pat. No. 4,962,095) and zofenopril (U.S. Pat. No. 4,931,464). However, amiodarone is a difficult drug to manage because of its numerous side effects, some of which are serious.

Amiodarone has several potentially fatal toxicities, the most important of which is pulmonary toxicity (hypersensitivity pneumonitis or interstitial/alveolar pneumonitis). Pulmonary toxicity is reversible if the progression of the symptoms is recognized on time, but is still fatal 10% of the time (Kerr et al., [1996], In *Cardiovascular Drug Therapy*, $2^{nd}$ ed., Editor: Messerli, F. H. W. B. Saunders Co. pp. 1247–1264; Vrobel et al., [1989] *Progr. In Cardiovasc. Dis.*, 31:393). Liver injury is also common but usually mild, although liver disease can occur and has been fatal in some cases. Even though toxicity is usually reversible upon cessation of drug administration, the real danger with amiodarone comes from its slow kinetics, especially slow elimination. For example, although the frequency of pro-arrhythmic events associated with amiodarone appears to be less than with other anti-arrhythmic agents (2 to 5%), the effects are prolonged when they occur. Even in patients at high risk of sudden death, in whom the toxicity of amiodarone is an acceptable risk, amiodarone poses major management problems that could be life-threatening, so every effort is made to utilize alternative agents first.

The most serious long-term toxicity of amiodarone derives from its kinetics of distribution and elimination. It is absorbed slowly, with a low bioavailability and relatively long half-life. These characteristics have clinically important consequences, including the necessity of giving loading doses, a delay in the achievement of full anti-arrhythmic effects, and a protracted period of elimination of the drug after its administration has been discontinued.

Amiodarone can also interact negatively with numerous drugs including aprindine, digoxin, flecainide, phenytoin, procainamide, quinidine, and warfarin. It also has pharmacodynamic interactions with catecholamines, diltiazem, propranolol, and quinidine, resulting in alpha- and beta-antagonism, sinus arrest and hypotension, bradycardia and sinus arrest, and torsades de pointes and ventricular tachycardias, respectively. There is also evidence that amiodarone depresses vitamin K-dependent clotting factors, thereby enhancing the anticoagulant effect of warfarin.

Numerous adverse effects limit the clinical applicability of amiodarone. Important side effects can occur including corneal microdeposits, hyperthyroidism, hypothyroidism, hepatic dysfunction, pulmonary alveolitis, photosensitivity, dermatitis, bluish discoloration, and peripheral neuropathy.

There is no Class-III agent presently marketed that can be used safely in patients with CHF. The cardiovascular drug market is the largest in any field of drug research, and an effective and safe Class-III anti-arrhythmic agent useful in patients with CHF is expected to be of substantial benefit. Therefore, a drug which could successfully improve the prognosis of CHF patients, but with a safety profile much improved over that of amiodarone, would be extremely useful and desired.

U.S. Pat. Nos. 5,364,880; 5,440,054; and 5,849,788 (all to Druzgala) disclose novel anti-arrhythmic amiodarone analogs which are metabolized by esterases. The 2-butyl chain of amiodarone was functionalized to include an ester moiety, thus allowing endogenous esterases to metabolize the compounds into a primary metabolite containing a carboxylic acid moiety. Advantages associated with these compounds include smaller distribution volumes, shorter onset of activity, faster elimination rates, and safer long-term toxicity profiles. These amiodarone derivatives were synthesized as racemic mixtures.

The observed pharmacological activity of a given compound is the result of a complex interaction between its intrinsic activity at receptor level, its physical properties that determine transport through biological membranes, and its affinity toward metabolizing enzymes. As a result of this, it is practically impossible to predict differences in pharmacological activities between compounds that have very similar structures and similar physicochemical properties, such as optical isomers.

Biological systems however, because they are made of an assemblage of chiral subunits, are capable of recognizing optical isomers. The direct consequence of this chirality is often expressed by differences in receptor affinity, resulting in widely different pharmacological activities between optical isomers of the same drug. One of the most striking examples in the anti-arrhythmic field is the difference in pharmacological activity between d- and l-sotalol. Whereas d-sotalol is a class-III anti-arrhythmic, l-sotalol is a beta-blocker that is devoid of class-III properties. Clinical trials have demonstrated that neither d- nor l-sotalol alone are sufficient for efficient anti-arrhythmic activity in man, but that the mixture d, l-sotalol is required.

BRIEF SUMMARY OF THE INVENTION

The subject invention pertains to novel enantiomerically pure compounds, and compositions comprising the compounds, for the treatment of cardiac arrhythmias. The subject invention further concerns a method of making and purifying the compounds. The isolated enantiomerically purified compounds and compositions of these compounds exhibit unexpectedly distinct and advantageous characteristics, such as a markedly superior ability to reduce or inhibit ventricular premature beats, as compared to racemic mixtures of the compounds.

The enantiomerically pure compounds of the subject invention show differences at the kinetic and the dynamic levels that were totally unpredictable a priori. These pharmacological properties provide for the ability to reduce undesirable side effects associated with anti-arrhythmic drugs while maintaining a superior ability to modulate cardiac function in treatment regimens.

DETAILED DISCLOSURE OF THE INVENTION

Figure 1:
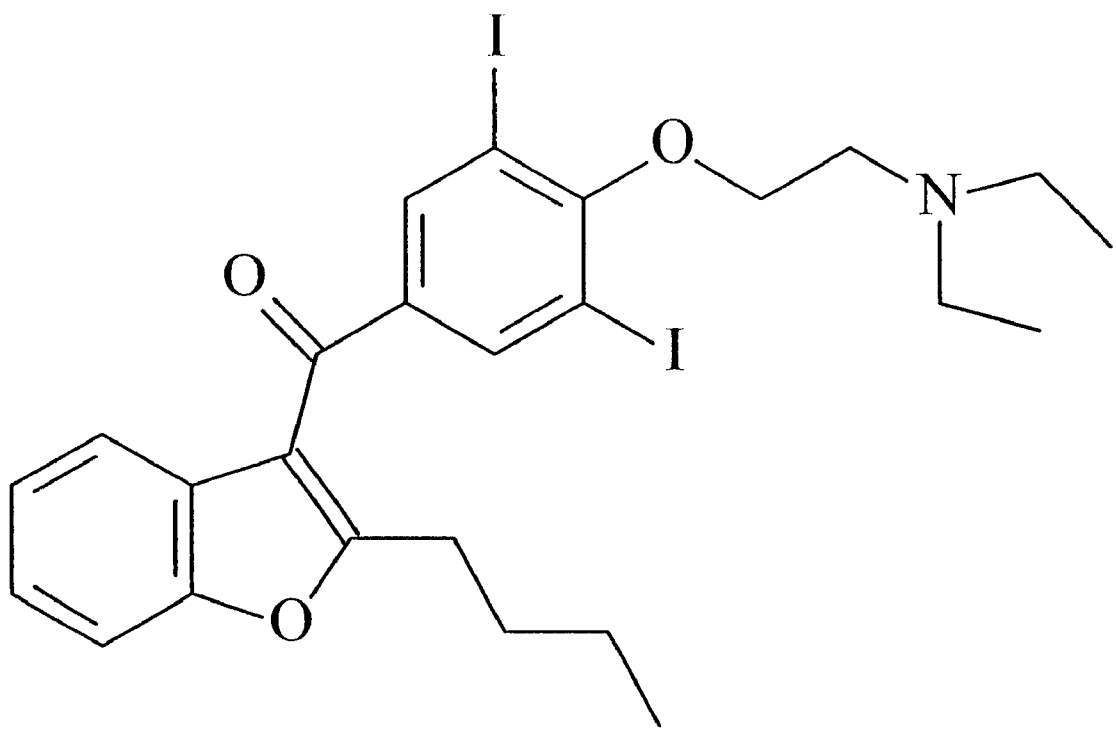
FIG. 1 depicts amiodarone.

The subject invention pertains to enantiomerically isolated compounds, and compositions comprising the compounds, for the treatment of cardiac arrhythmias. The subject invention further concerns methods of making and purifying the compounds. The isolated enantiomerically pure compounds, and compositions of these compounds, exhibit unexpectedly distinct and advantageous characteristics, such as a markedly superior ability to reduce or inhibit ventricular premature beats as compared to racemic mixtures of the compounds.

The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least about 99% enantiomeric excess.

The improved properties, or characteristics, of the compounds of the subject invention provide for improved methods of treating cardiac arrhythmias by administering the compounds of the invention to an individual in need of treatment. One or more compounds of the invention may be administered to an individual. Furthermore, the compounds of the invention may be administered in conjunction with other compounds, or compositions thereof. These compounds, and compositions thereof, may include other compounds known to be useful for the treatment of cardiac arrhythmias, cardioprotective agents, antibiotics, antiviral agents, or thrombolytic agents (e.g., streptokinase, tissue plasminogen activator, or recombinant tissue plasminogen activator).

The compounds and compositions of the invention can have particular usefulness for treating life-threatening ventricular tachyarrhythmias, especially in patients with congestive heart failure (CHF). Post-myocardial infarction patients can also particularly benefit from the administration of the subject compounds and compositions; thus, methods of treating post-myocardial infarction patients are also provided by the subject invention. An "individual" includes animals and humans in need of treatement for arrythmias. In a preferred embodiment, the individual is a human.

Cardioprotective agents include vasodilators and beta blockers described for use in patients with coronary insufficiency (such as those of U.S. Pat. No. 5,175,187 or others known to the skilled artisan). Other cardioprotective agents include known anti-hypertensive agents, e.g., (S)-1-[6-amino-2-[[hydroxy(4-phenylbutyl)phosphinyl]oxyl]-L-proline (U.S. Pat. No. 4,962,095) and zofenopril (U.S. Pat. No. 4,931,464). Additional cardioprotective agents include, but are not limited to, aspirin, heparin, warfarin, digitalis, digitoxin, nitroglycerin, isosorbide dinitrate, hydralazine, nitroprusside, captopril, enalapril, and lisinopril.

The compounds and compositions also provide effective management for ventricular arrhythmias and supraventricular arrhythmias, including atrial fibrillation and re-entrant tachyarrhythmias involving accessory pathways. Compounds and compositions of the invention are also useful for the treatment of ventricular and supra-ventricular arrhythmias, including atrial fibrillation and flutter, paroxysmal supraventricular tachycardia, ventricular premature beats (VPB), sustained and non-sustained ventricular tachycardia (VT), and ventricular fibrillation (VF). Other non-limiting examples of the arrhythmias which may be treated by the compounds of the instant invention include: narrow QRS tachycardia (atrial, intra-/para-A-V node, or accessory pathway), ventricular tachycardia, and ventricular arrhythmias in cardiomyopathy.

Thus, the subject invention represents an innovative improvement of a Class-III anti-arrhythmic agent having significantly lower toxicity than any currently available compound. The compounds and compositions are useful for treating patients with congestive heart failure (CHF) and exhibit fewer undesirable properties as compared to racemic mixtures of the compounds.

Thus, the invention provides isolated enantiomeric compounds of the formulae:

(S-2042 Series)

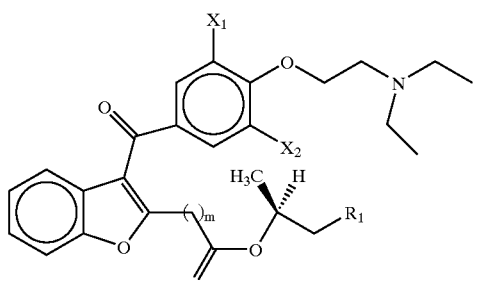

(R-2042 Series)

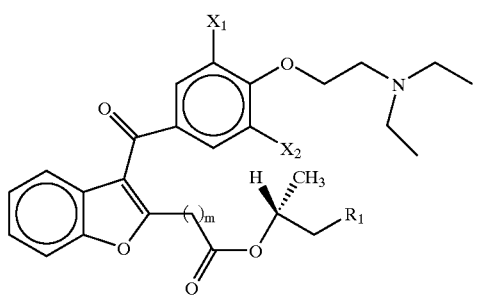

(S-2055 Series)

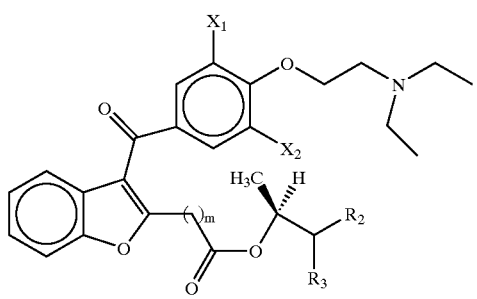

(R-2055 Series)

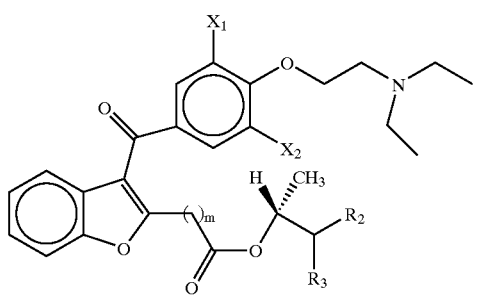

wherein
- $X_1$ and $X_2$ may be the same or different and are selected from the group consisting of iodine, fluorine, bromine, and chlorine;
- $R_1$, $R_2$, and/or $R_3$ is a moiety selected from the group consisting of H, $C_{n-20}$ alkyl, $C_{2-20}$ alkenyl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with moiety selected from the group consisting of $C_{1-6}$ alkyl, halogen, CN, $NO_2$, and $SO_{2-4}$.

In accordance with the subject invention, m may be from 0 to 10. In a preferred embodiment, m is 4. In another preferred embodiment, m is 3. In a more preferred embodiment, m is 2. In an even more preferred embodiment, m is 0. In the most preferred embodiment, m is 1.

As used in this specification the term "$C_{n-20}$ alkyl" refers to straight or branched chain alkyl moiety having up to twenty carbon atoms, including for example, methyl, ethyl, propyl, isopropyl, butyl, tert-butyl, pentyl, hexyl and the like. The value for n may be from 1 to 19. In one embodiment, n is 1, in a preferred embodiment, n is 2.

The term "$C_{2-20}$ alkenyl" refers to a straight or branched chain alkyl moiety having two to twenty carbon atoms and having in addition at least one double bond. This term includes for example, vinyl, 1-propenyl, 1- and 2-butenyl, 2-methyl-2-propenyl, etc.

The term "cycloalkyl" refers to a saturated alicyclic moiety having from three to six carbon atoms and which is optionally benzofused at any available position. This term includes, for example, cyclopropyl, cyclobutyl, cyclopentyl, cyclohexyl, indanyl and tetrahydronaphthyl.

The term "heterocycloalkyl" refers to a saturated heterocyclic moiety having from three to six atoms including one or more heteroatoms selected from N, O, S and oxidized versions thereof, and which is optionally benzofused at any available position. This term includes, for example, azetidinyl, pyrrolidinyl, tetrahydrofuranyl, piperidinyl, indolinyl and tetrahydroquinolinyl.

The term "cycloalkenyl" refers to an alicyclic moiety having from three to six carbon atoms and having in addition at least one double bond. This term includes, for example, cyclopentenyl and cyclohexenyl.

The term "heterocycloalkenyl" refers to an alicyclic moiety having from three to six atoms and one or more heteroatoms selected from N, O, S and oxidized versions thereof, and having in addition at least one double bond. This term includes, for example, dihydropyranyl.

The term "aryl" refers to an aromatic carbocyclic radical having a single ring or two condensed rings. This term includes, for example phenyl or naphthyl.

The term "heteroaryl" refers to an aromatic ring system of five to ten atoms of which at least one atom is selected from O, N and S, and includes, for example, furanyl, thiophenyl, pyridyl, indolyl, quinolyl and the like.

The term "cycloimidyl" refers to a saturated ring of five to ten atoms containing the atom sequence —C(=O)NC(=O)—. The ring may be optionally benzofused at any available position. Examples include succinimidoyl, phthalimidoyl and hydantoinyl.

The term "benzofused" refers to the addition of a benzene ring sharing a common bond with the defined ring system.

The term "optionally substituted" means optionally substituted with one or more of the groups specified, at any available position or positions.

The term "halogen" means fluorine, chlorine, bromine or iodine.

The subject invention also provides compositions containing the compounds of the invention in pharmaceutically acceptable carriers. The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In one aspect, the subject invention provides pharmaceutical compositions comprising, as an active ingredient, an effective amount of one or more of the compounds and one or more non-toxic, pharmaceutically acceptable carriers or diluents. Examples of such carriers for use in the invention include ethanol, dimethyl sulfoxide, glycerol, silica, alumina, starch, and equivalent carriers and diluents.

Further, acceptable carriers can be either solid or liquid. Solid form preparations include powders, tablets, pills, capsules, cachets, suppositories and dispersible granules. A solid carrier can be one or more substances which may act as diluents, flavoring agents, solubilizers, lubricants, suspending agents, binders, preservatives, tablet disintegrating agents or an encapsulating material.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampules. Also, the unit dosage can be a liquid based preparation or formulated to be incorporated into solid food products, chewing gum, or lozenges.

The dosage administered to an individual will be dependent upon the response desired and may be dependent upon the type of host involved, its age, health, weight, kind of concurrent treatment, if any; frequency of treatment; therapeutic ratio and like considerations. Advantageously, dosage levels of the administered active ingredients can be, for examples, dermal, 1 to about 500 mg/kg; orally, 0.01 to 200 mg/kg; intranasal 0.01 to about 100 mg/kg; and aerosol 0.01 to about 50 mg/kg of body weight.

Expressed in terms of concentration, the isolated enatiomeric forms of the invention can be present in the new compositions for use dermally, intranasally, bronchially, intramuscularly, intravaginally, intravenously, or orally in a concentration of from about 0.01 to about 50% (w/w) of the composition, and especially from about 0.1 to about 30% (w/w) of the composition. Preferably, the isolated enantiomeric forms of the compounds are present in a composition from about 1 to about 10% (w/w). In one embodiment, the composition comprises about 5% (w/w) of the isolated enantiomeric compound.

In other embodiments, the compounds of the subject invention are administered intravenously and/or orally. Initial oral "loading doses" are, typically, administered over the course of one to three weeks. The loading doses may be administered over longer or shorter time frames and are administered until an initial therapeutic effect is observed. Typically, individual patient titration is performed for the administration of the subject compounds (i.e., the therapeutic regimen is tailored to a specific patient).

The following dosage ranges represent suggested guidelines for the oral and intravenous administration of the subject compounds to an individual. Initial loading doses range between 100 and 5000 mg per day, preferably between 250 and 4000 mg per day, more preferably between 400 and 3000 mg per day, even more preferably between 600 and 2000 mg per day, and most preferably between 700 and 1600 mg per day.

After adequate arrhythmia control is established, the dosage of the compounds of the subject invention may be reduced over the course of about one month. Dosages administered over this time frame are between 100 and 1600 mg per day, preferably between 200 and 1400 mg per day, more preferably between 300 and 1200 mg per day, even more preferably between 400 and 1000 mg per day, and most preferably between 600 and 800 mg per day.

After this reduction in compound dosage, individuals are typically maintained on compound dosages of about 400 mg per day (the maintenance dosage). Because control of arrhythmias is patient specific, some maintenance dosages may be higher or lower than the typical maintenance dosage. Thus, maintenance dosages can range between 50 and 800 mg per day, preferably between 100 and 700 mg per day, even more preferably 200 and 600 mg per day, and most preferably between 300 and 500 mg per day.

The invention also provides for salts of the disclosed compounds. Salts of the compounds include pharmaceutically acceptable salts, for example acid addition salts derived from inorganic or organic acids, such as hydrohlorides, hydrobromides, p-toluenesulfonates, phosphates, sulfates, perchlorates, acetates, trifluororacetates, proprionates, citrates, malonates, succinates, lactates, oxalates, tatrates, and benzoates. Salts may also be derived from bases (organic and inorganic), such as alkali metal salts (e.g., magnesium or calcium salts), or organic amine salts, such as morpholine, piperidine, dimethylamine, or diethylamine salts.

Table 1 provides the electrophysiological activities of the individual enatiomers as compared to each respective racemate. The descriptors "longer", "shorter", "higher", "lower", or "no change" describe the electrophysiological effects of the isolated enatiomers as compared to the respective racemate. This table summarizes the data provided in Examples 3–6 and FIGS. 2–12.

TABLE 1

|  | R-2042 | S-2042 | R-2055 | S-2055 |
| --- | --- | --- | --- | --- |
| Inhibition of VPB | longer | longer | longer | longer |
| Number of VPB | lower | lower | lower | lower |
| Inhibition of tachycardia | longer | longer | longer | longer |
| Heart rate (beats/minute) | lower | lower | lower | lower |
| QT interval | no change | longer | no change | no change |
| QRS interval | no change | longer | longer | longer |
| PR interval | shorter | longer | shorter | shorter |
| Plasma half-life (hours) | 5.0 | 7.3 | 11.7 | 8.8 |

All publications, patents and patent applications cited herein, whether supra or infra, are hereby incorporated by reference in their entirety to the extent that the reference is not inconsistent with the teachings provided herein. Following are examples which illustrate procedures for practicing the invention. These examples should not be construed as limiting. All percentages are by weight and all solvent mixture proportions are by volume unless otherwise noted.

EXAMPLE 1

Anti-arrhythmic Activity in Anesthetized Rats

Male Sprague-Dawley rats with body weights of 410±30 g (Harlan Sprague Dawley Inc., Indianapolis, Ind.), were anesthetized with sodium pentobarbital (50 mg/kg i.p.—Butler Co., Columbus, Ohio). The skin from the neck area was removed and the jugular veins on both sides were cleared of connective tissue. Both jugular veins and the left carotid artery were isolated, and the latter tied up cranially with a surgical silk (ETHICON 4-0, Ethicon Inc., Australia). A plastic catheter (INTRACATH 19 ga, Vecton Dickinson, Sandy, Utah), filled with a solution containing 10% sodium heparin (Elkins-Sinn Inc., Cherry Hill, N.J.) in normal saline (100 U/ml sodium heparin), was introduced into the artery and fixed with surgical silk.

The catheter was connected to a pressure transducer (OHMEDA P23-XL, Ohmeda Medical Devices Division Inc., Madison, Wis.), filled with the same heparinized 0.9% NaCl solution, to register beat-to-beat arterial pressure. Needle electrodes were inserted s.c., and together with the pressure transducer, were joined to a GOULD TA 2000 recorder. Leads II, aVF and intraarterial blood pressure were monitored simultaneously throughout the experiments and recorded at certain intervals at 50 and 200 mm/sec paper speed.

The surgery was completed with an incision on the trachea where a short plastic tubing was placed and the animal was connected to a rodent-model ventilator (HARVARD Model 683, Harvard Apparatus, Inc., Holliston, Mass.). The animals were ventilated in a controlled way, depending on their spontaneous breathing frequency (55–75/min).

Drug administrations were carried out through i.v. catheters (TERUMO 24 GA*¾", Terumo Medical Corp., Elkton, Md.) inserted into both jugular veins. The left side was used for drug infusions by means of a syringe pump (SAGE INSTRUMENTS, Model 341B, Orion Res. Inc., Boston, Mass.), and the right side was used for adrenaline injections. The experiments were started after at least 15 minutes of stabilization. Benzene/adrenaline challenges were performed as follows: the respirator inlet was connected to a 50-ml bubbler half-full with benzene (Fisher Scientific, Fair Lawn, NJ) so that the inspired air was saturated with benzene vapor. The animal was ventilated with benzene vapor for two minutes. The tidal volume was typically 1 ml/100 g of animal. During the last 30 seconds of benzene ventilation, 10 $\mu$g/kg adrenaline solution (in 0.9% NaCl) was injected into the right jugular vein. Typically, within 30 seconds, ventricular premature beats (VPB) and hemodynamically stable sustained and non-sustained repetitive rhythm returned and the animal did not show other abnormal signs. These arrhythmias could be elicited repeatedly. After three control VTs (at –30, –20 and –10 minutes), the test compounds were injected slowly during 30 seconds at a dose of 4 mg/kg i.v., immediately followed by a slow infusion of 12 mg/kg/h for 2 hours. The flow rate during the infusion period was 1 ml/h.

There were 5 rats per test compound and each animal served as its own control. The ability of the different drugs to suppress arrhythmias was tested against repeated benzene/adrenaline challenges at 5, 15, 30, 45, 60, 90, 120 (end of drug infusion), 135, 150, 165 and 180 minutes after the i.v. bolus injection. The amplitudes of the systolic arterial pressure and diastolic arterial pressure were DBP/3+DBP with the help of a pressure-amplitude calibration curve. Heart rate, number of ventricular complexes during the occurrence of VTs and VPBs, and certain ECG parameters (PR, QRS, QT durations and RR cycle lengths in msec) were also recorded and measured manually. At each time-point, 3–5 cycles were measured and the average values were entered into EXCEL Windows 97. The average and standard deviation for the five experimental animals per compound were calculated. Results are shown in FIGS. 2–11.

EXAMPLE 2

Half-life in Human Plasma in vitro

Venous blood (60 ml) was collected in heparinized 15-ml Vacutainer® tubes from the forearm of five human volunteers. Each tube contained 1,000 units of heparin sodium salt. The blood was immediately centrifuged at 2,000 g for 10 minutes and the plasma was collected. Immediately after collection, the plasma was divided into 2-ml aliquots in borosilicate glass tubes (5-ml capacity) capped with a plastic stopper. The tubes were then equilibrated in a 37° C.-water bath for at least 15 minutes before the test samples were added.

Stock solutions were prepared by dissolving 25 $\mu$moles (about 18 mg) of each of the test compounds in 10 ml of deionized water. To each of the glass tubes containing 2 ml of fresh plasma, equilibrated at 37° C., was added 40 $\mu$l of the stock solutions (one test compound per tube). The plasma/stock solutions were then mixed. Samples (250 $\mu$l) were collected at time 0 (immediately after mixing test compounds in plasma) and then at 30, 60, 90, 120, 180, 240, and 300 minutes. The test tubes were capped, to avoid concentration due to evaporation, and left in the 37° C. bath during the entire experiment. Each aliquot was immediately introduced into a 1.5-ml microfuge tube containing 20 $\mu$l of a 0.01% solution of diethyl paranitrophenylphosphate (paraoxon) in ethanol in order to inhibit esterase activity. The tubes were then capped and vortexed, then kept at –20° C. until analysis. The samples were thawed and mixed with 750 $\mu$l of a 0.1% solution of trifluoroacetic acid (TFA) in acetonitrile, vortexed for thorough mixing, and then centrifuged at 12,000 g for 15 minutes. The supernatant was collected for injection in the HPLC system.

Figure 12:
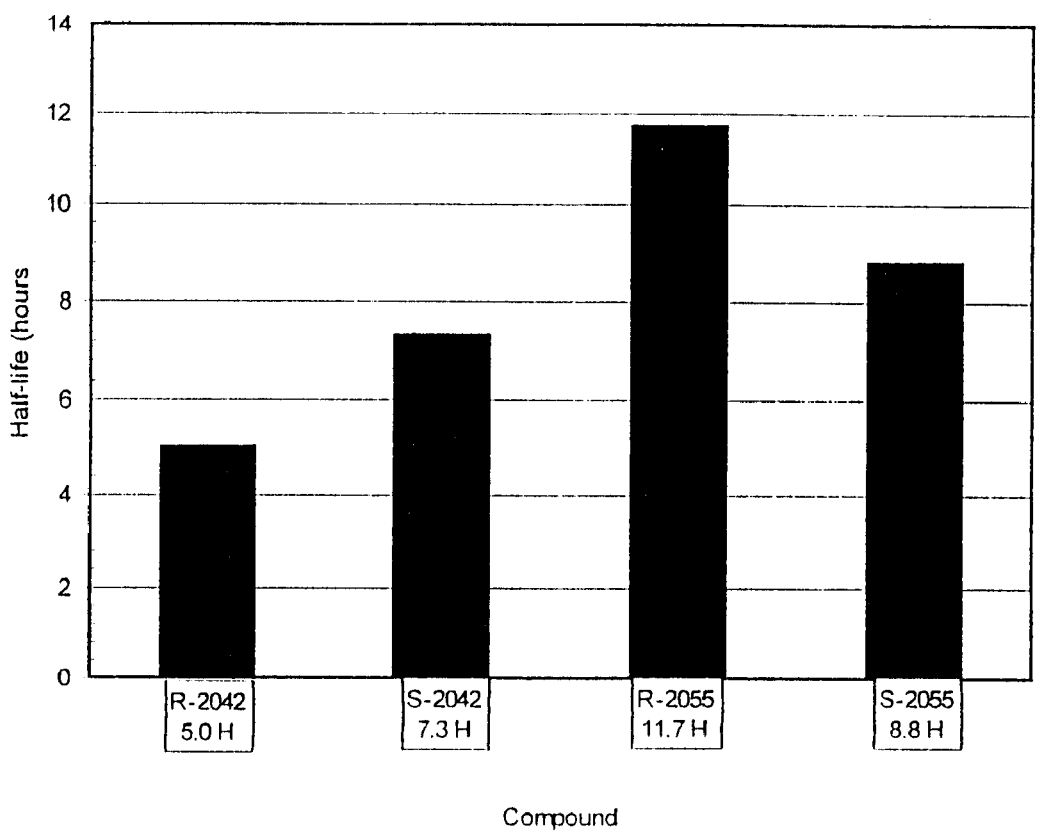
FIG. 12 illustrates the plasma half-life of the compounds.

The HPLC mobile phase consisted of acetonitrile and water containing 0.1% TFA and 400 mg/L benzyltriethylammonium chloride (BTEAC) in the following proportions and flow rates: 85% acetonitrile and 15% water at 2.0 ml/min. The detection wavelength was set at 242 nm, and the injected volume was 100 $\mu$L. The HPLC peaks were recorded, and the integrated values were plotted against time using the SIGMAPLOT software version 4.0 for WINDOWS. The resulting curves were fitted to a first-order exponential decay equation from which hydrolysis half-lives were calculated. Half-life in human plasma is shown in FIG. 12.

EXAMPLE 3

ATI-2042: Electrophysiological Properties in Anesthetized Rats

Figure 2:
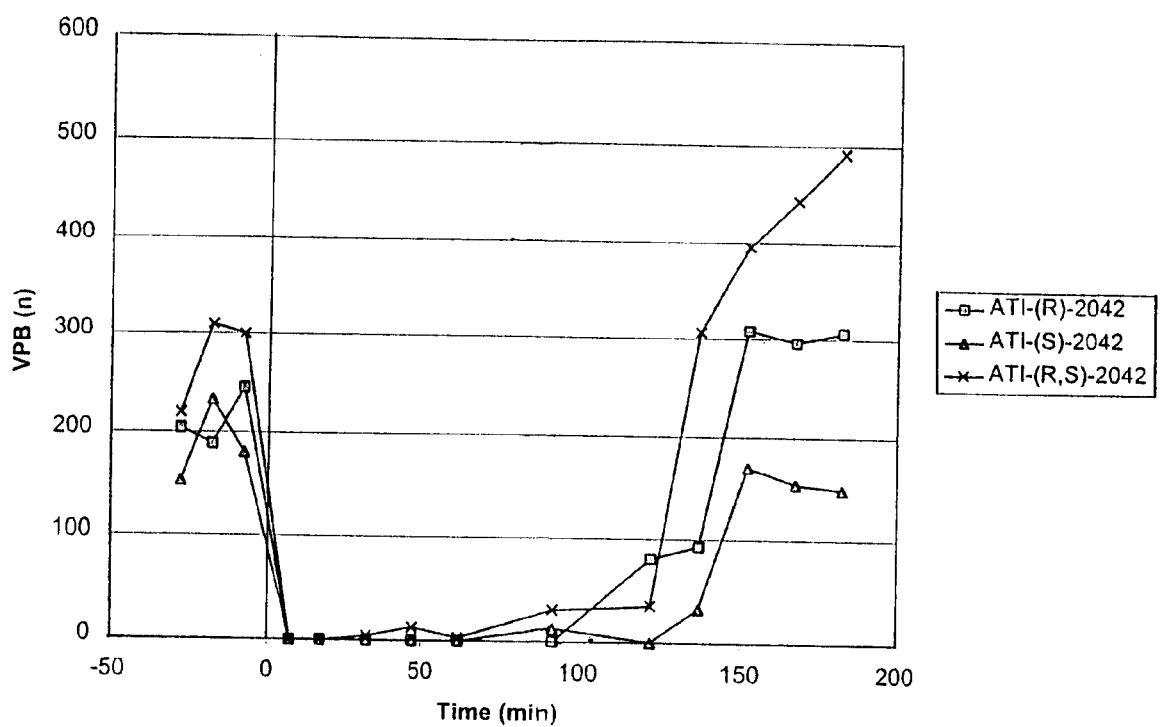
FIG. 2 depicts the anti-arrhythmic activity of the test compounds R-2042, S-2042, and the racemate R,S-2042 by measuring their ability to inhibit the formation of extrasystoles or ventricular premature beats (VPB) when rats are challenged by an arrhythmogenic combination of benzene vapors and adrenaline.
Figure 3:
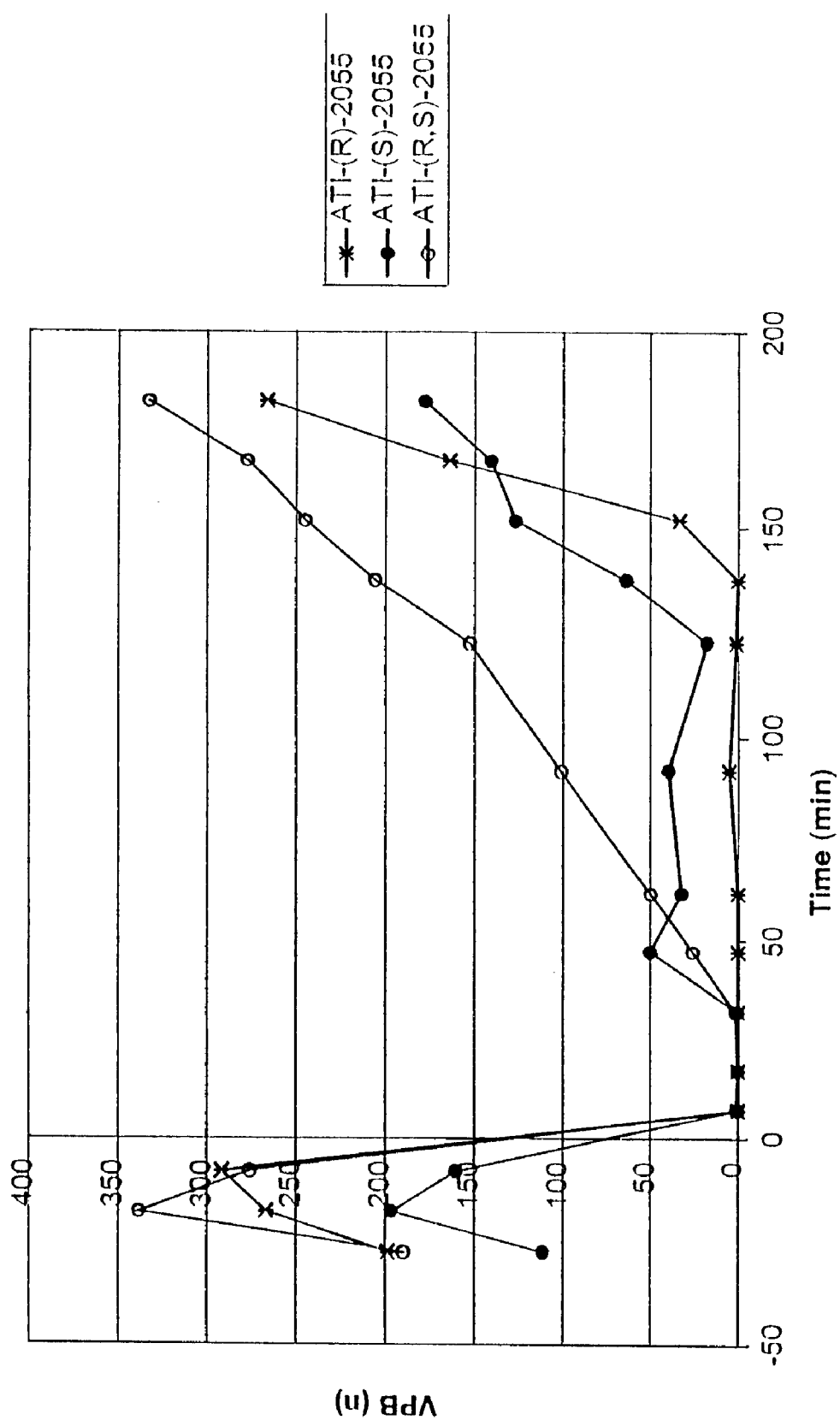
FIG. 3 demonstrates the anti-arrhythmic activity of the test compounds R-2055, S-2055, and the racemate R,S-2055 by measuring their ability to inhibit the formation of extrasystoles or ventricular premature beats (VPB) when rats are challenged by an arrhythmogenic combination of benzene vapors and adrenaline.

In anesthetized rats, there is a marked difference in pharmacological activity between R-2042, S-2042, and the racemate R,S-2042. In FIG. 2, we measured the antiarrhythmic activity of the test compounds by measuring their ability to inhibit the formation of extrasystoles or ventricular premature beats (VPB) when the rats were challenged by an arrhythmogenic combination of benzene vapors and adrenaline. While S-2042 totally inhibited the formation of ventricular premature beats for the whole period of drug administration (time 0 to 120 min) and still retained part of its activity at the end of the washout period (time 180 min), R-2042 loses activity much sooner (around time 100 min) and is completely inactive at the end of the washout period. The racemate R,S-2042 is even less active than either the R- or the S-isomer.

Figure 4:
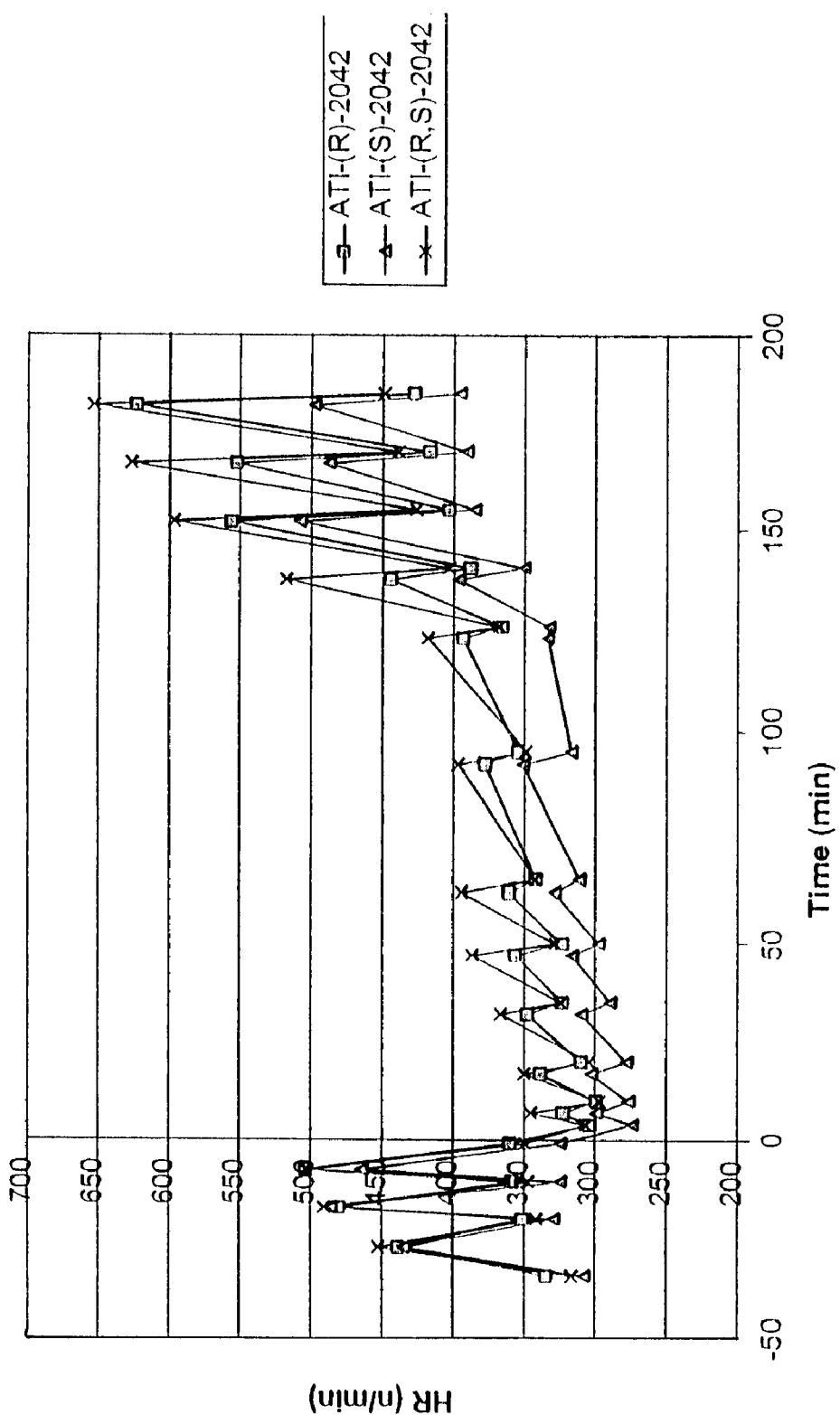
FIG. 4 illustrates the change of heart rate in animals injected with adrenaline and the anti-tachyarrhythmic properties of test compounds R-2042, S-2042, and the racemate R,S-2042.
Figure 5:
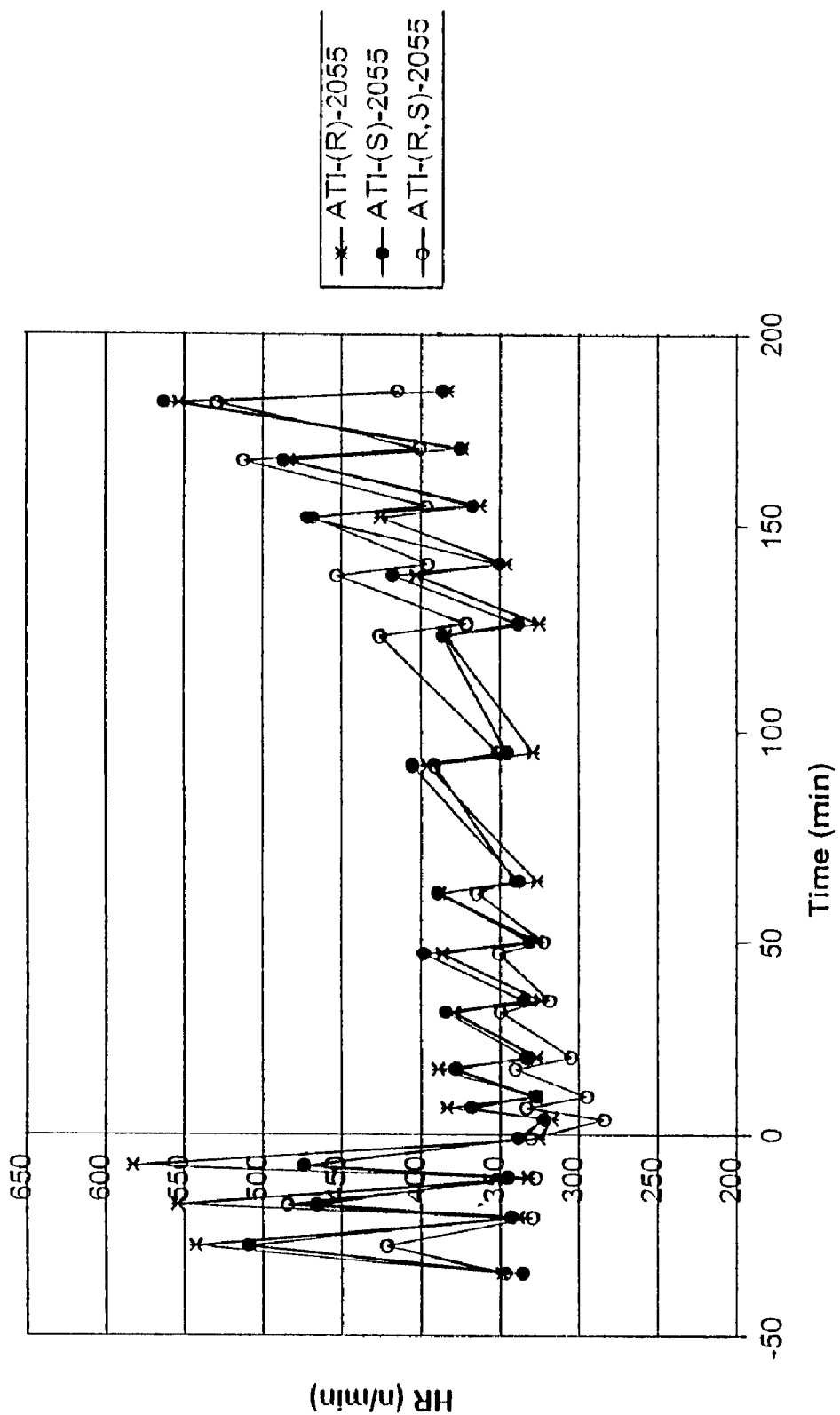
FIG. 5 shows the change of heart rate in animals injected with adrenaline and the anti-tachyarrhythmic properties of test compounds R-2055, S-2055, and the racemate R,S-2055.

FIG. 4 shows how the heart rate suddenly increases from 320 beats per minute (bpm) to between 500 and 600 bpm when the rats are injected with adrenaline. When ATI-2042 is administered from time 0 to time 120 minutes, we observe a very good protection against this tachyarrhythmia. However, as in FIG. 2, S-2042 is more potent and longer acting then R-2042, the racemic mixture R,S-2042 being the least potent and shortest acting. The same trend is observed in FIGS. 6, 8, and 10.

Figure 6:
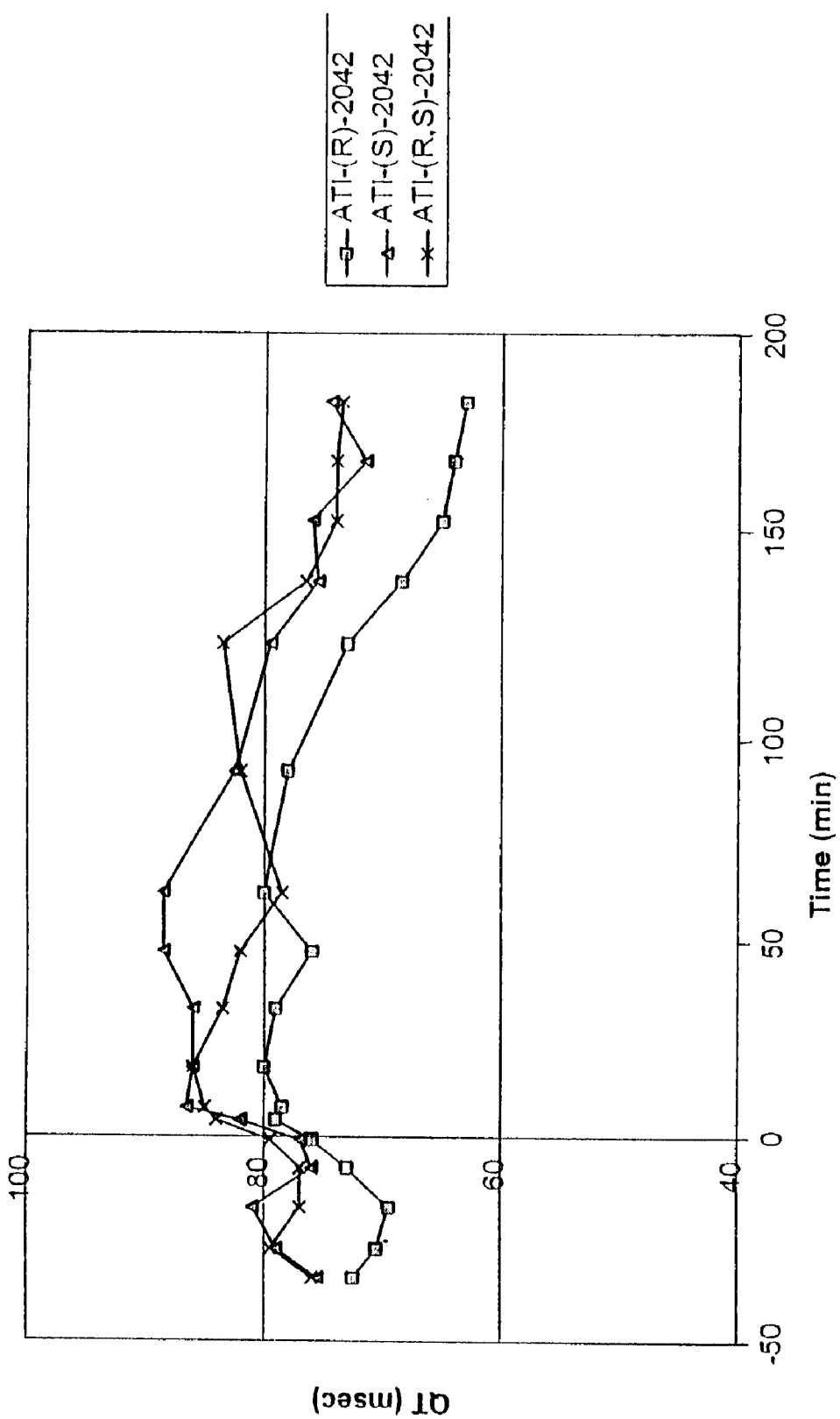
FIG. 6 depicts the ability of test compounds R-2042, S-2042, and the racemate R,S-2042 to modulate the QT segment of EKG measurements.
Figure 8:
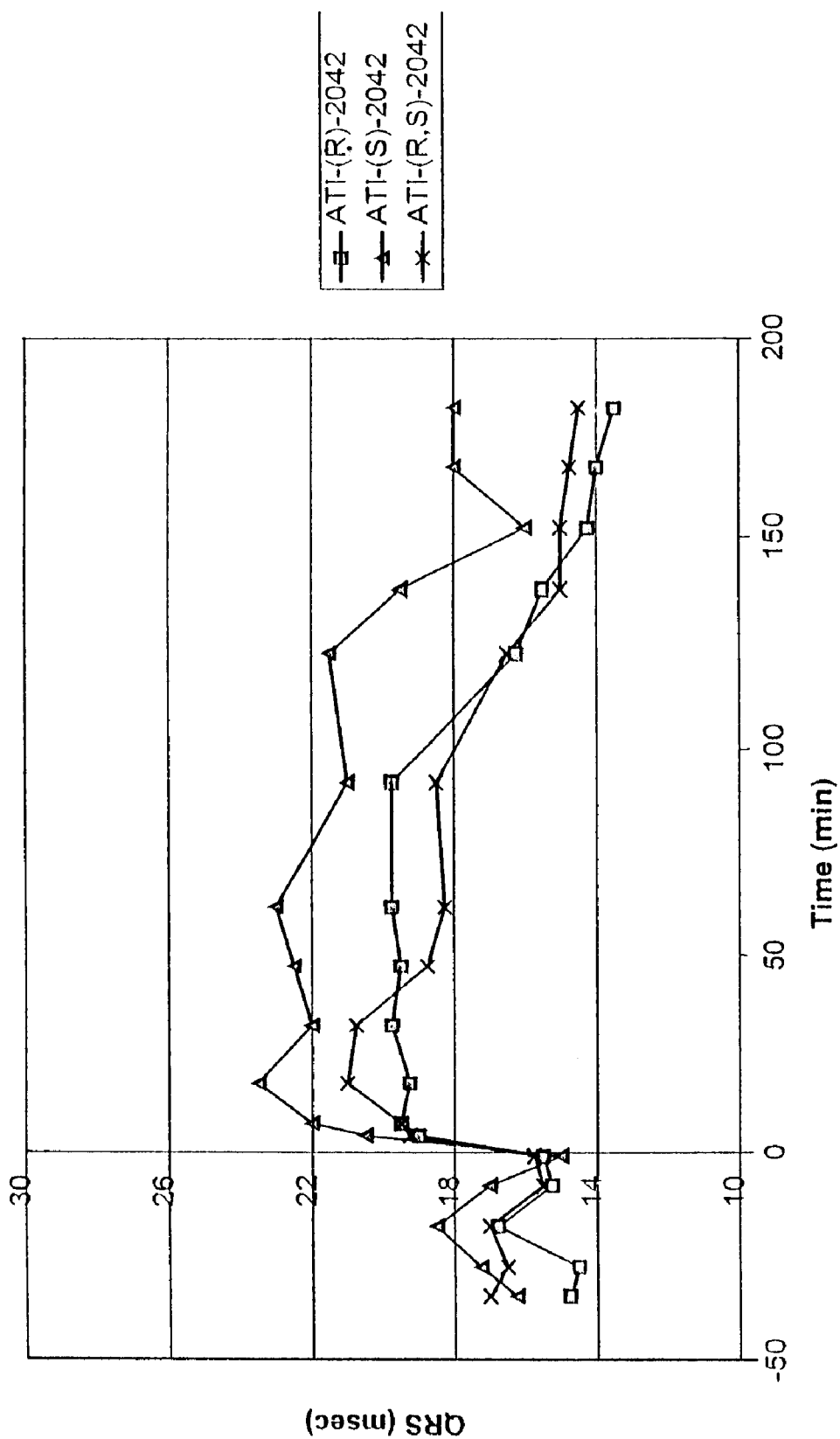
FIG. 8 illustrates the ability of test compounds R-2042, S-2042, and the racemate R,S-2042 to modulate the QRS segment of EKG measurements.
Figure 9:
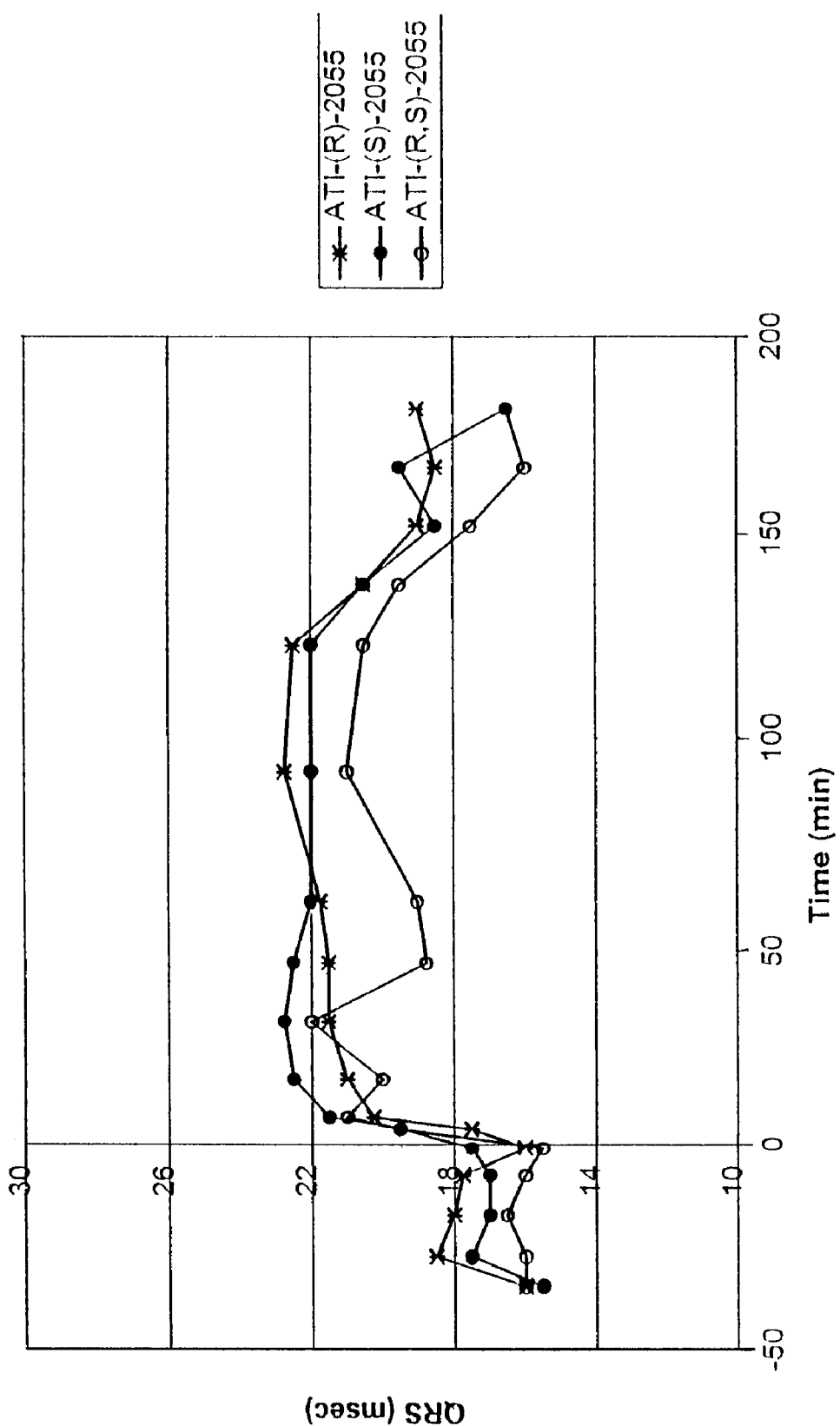
FIG. 9 shows the ability of test compounds R-2055, S-2055, and the racemate R,S-2055 to modulate the QRS segment of EKG measurements.

In FIG. 6, we see the effects of ATI-2042 on the QT segment of the EKG recording. This QT segment is a measure of the Class-III properties (potassium-channel blocking and increase in refractoriness) of the compounds. Again, R-2042, S-2042, and R,S-2042 show 3 different profiles of activity, S-2042 being the most potent and the longest acting. FIG. 8 shows the activity on the QRS segment of the EKG recording which measures the Class-I activity (sodium-channel blocking and decreased conduction rate). Here again, the previous pattern between the individual isomers and the racemate is conserved.

Figure 10:
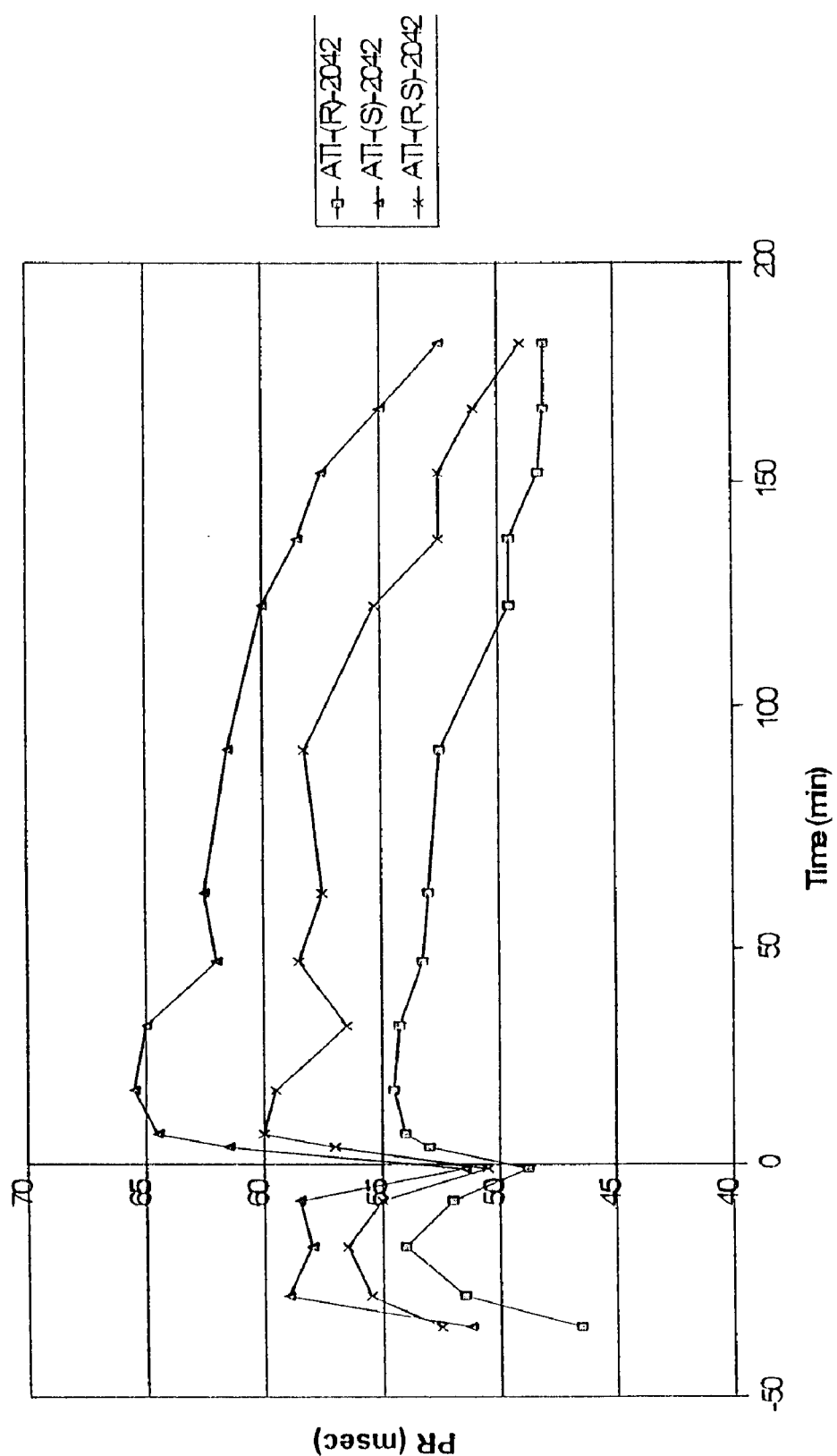
FIG. 10 demonstrates the ability of test compounds R-2042, S-2042, and the racemate R,S-2042 to modulate the PR segment of EKG measurements.
Figure 11:
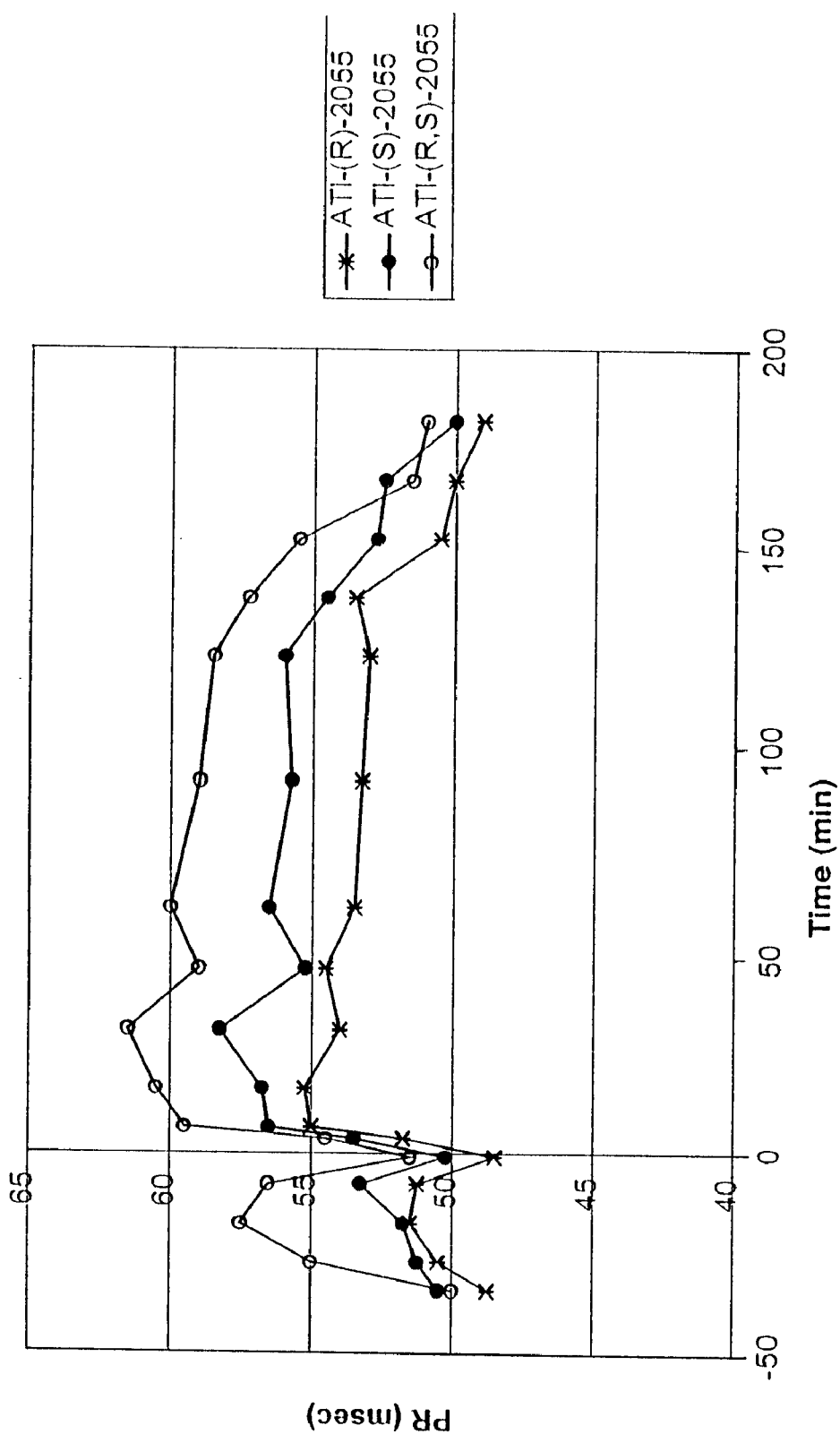
FIG. 11 depicts the ability of test compounds R-2055, S-2055, and the racemate R,S-2055 to modulate the PR segment of EKG measurements.

Finally, in FIG. 10, we see the effects on the PR segment of the EKG recording, which measures the Class-IV activity of the compounds (calcium-channel blocking and decreased AV conduction). Again, we see that in this model, S-2042 is much more potent than R-2042 and the racemate R,S-2042.

EXAMPLE 4

Half-life in Human Plasma in vitro

ATI-2042 is metabolized in human plasma by esterase enzymes. The half-life of the R-isomer is 5.0 hours whereas the S-isomer has a half-life of 7.3 hours, a substantial difference. The R-isomer is not always the most rapidly metabolized isomer in the ATI-2000 series (see FIG. 12).

EXAMPLE 5

ATI-2055: Electrophysiological Properties in Anesthetized Rats

In anesthetized rats, there were also differences in pharmacological activity between R-2055, S-2055, and the racemate R,S-2055. We measured the anti-arrhythmic activity of the test compounds by measuring their property to inhibit the formation of extrasystoles or ventricular premature beats (VPB) when the rats are challenged by an arrhythmogenic combination consisting of benzene vapors and adrenaline. While R-2055 totally inhibited the formation of ventricular premature beats for the whole period of drug administration (time 0 to 120 min) and still retained part of its activity at the end of the washout period (time 180 min), we see that S-2055 loses activity much sooner (about time 40 min) and is completely inactive at the end of the washout period. The racemate R,S-2055 is even less active than either the R-2055 or the S-2055 enantiomer (see FIG. 3). These differences in activity could not be predicted.

ATI-2055 inhibits the tachycardia (increased heart rate) produced by the injection of adrenaline. Whereas, the racemate R,S-2055 has a more potent effect than either R-2055 or S-2055, its effects wear off more rapidly, starting at about 50 minutes. Both R-2055 and S-2055 have similar potency, but R-2055 has a longer-lasting effect than S-2055 (see FIG. 5). Thus, using either of the enantiomers is preferable to using the racemate where a longer duration of action is a desired therapeutic effect.

Figure 7:
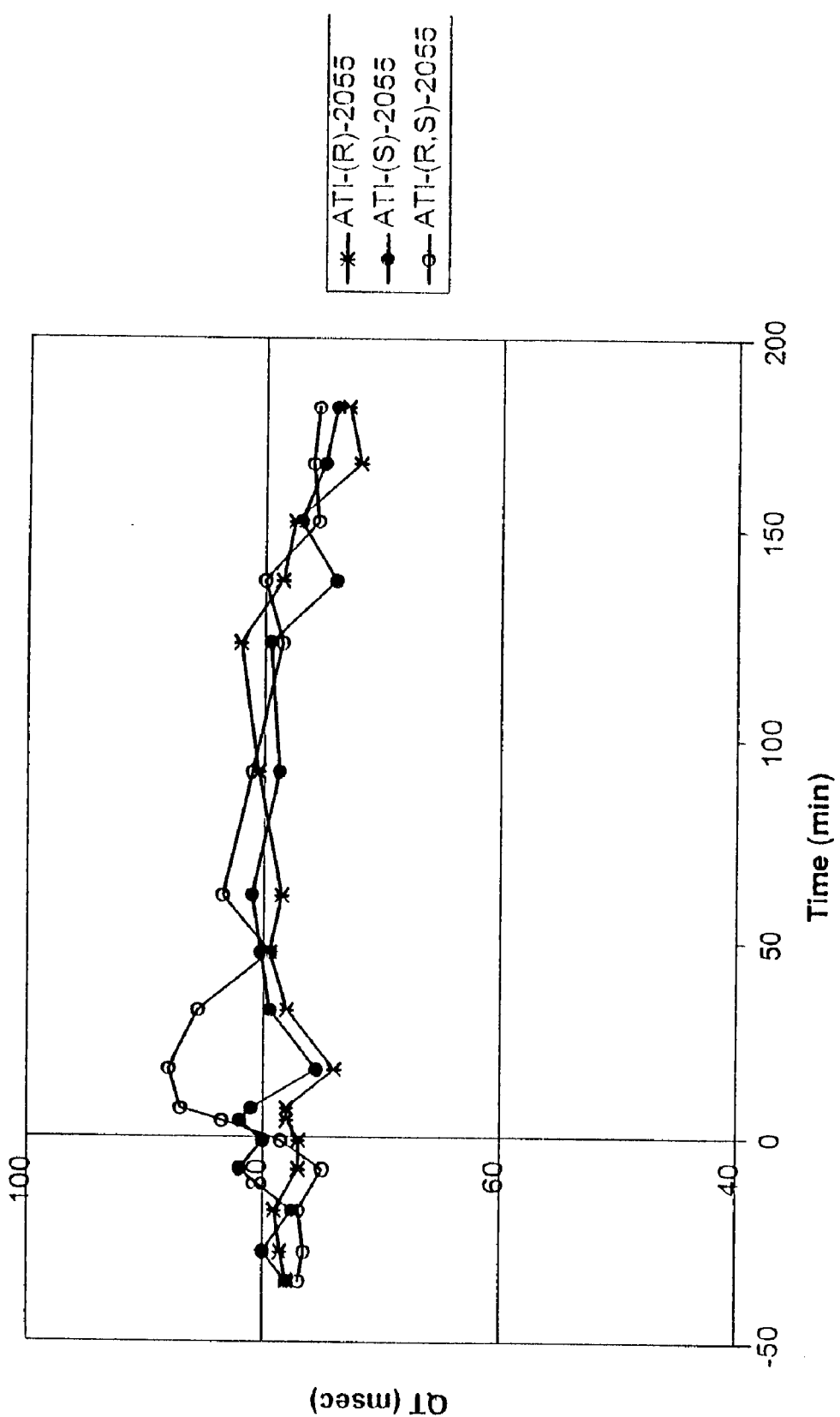
FIG. 7 demonstrates the ability of test compounds R-2055, S-2055, and the racemate R,S-2055 to modulate the QT segment of EKG measurements.

A similar trend is observed with the QT interval; the racemate is more potent than either one of the enantiomers, however, its duration of action is shorter (see FIG. 7). All three forms increase the QRS interval to a similar degree of potency, but again, the racemate has a shorter duration of action (see FIG. 9). All three forms also increase the P,R interval (see FIG. 11). The potency of the racemate is higher than would be expected from the potencies of the individual enantiomers, and this synergistic effect is a strong indication that the R- and S-enantiomers act at different calcium channel sites.

EXAMPLE 6

Half-life of ATI-2055 in Human Plasma in vitro

ATI-2055 is metabolized in human plasma by esterase enzymes (FIG. 12). The half-life of the R-isomer is 11.7 hours whereas the S-isomer has a half-life of 8.8 hours, a substantial difference. This is different from ATI-2042 where the R-isomer had a shorter half-life than the S-isomer and demonstrates the unpredictability associated with the relative enzymatic hydrolysis rates for the individual isomers of a chiral molecule.

EXAMPLE 7

Isolation/Production of ATI-2042 and ATI-2055 R and S Enantiomers 2-acetylbenzofuran (2). Potassium carbonate (588 g, 4.25 mol), acetone (1,000 ml), and salicylaldehyde (504 g, 4.13 mol) were introduced into a 5-liter 3-necked flask fitted with a mechanical stirrer, an addition funnel, and an efficient reflux condenser. Chloroacetone (388 g, 4.19 mol) was added slowly over a period of 60 minutes at such a rate that the reaction temperature never went out of control (a mild reflux was achieved after 30 minutes of chloroacetone addition). After the addition was complete, a mild reflux was maintained for another 120 minutes. The reaction was then allowed to cool down to room temperature and was filtered into another 5-liter flask. The potassium carbonate cake was washed with acetone (100 ml) and the solvent was evaporated. The crude product weighed 602 g and was used as such in the next step. The product was purified by vacuum distillation (bp 80°/1 mm). The pure product solidified as white needles melting at 71–72° C. Anal. ($C_{10}H_8O_2$) C, H: calculated 74.99, 5.03; found 74.95, 5.04.

2-benzofurylthioacetomorpholide (3). 2-Acetylbenzofuran (488 g, 3.05 mol), sulfur powder (98 g, 3.06 mol), and morpholine (285 g, 3.27 mol) were introduced into a 3-liter 3-necked flask fitted with a reflux condenser, a thermometer, and a mechanical stirrer. The mixture was brought to a gentle reflux (126–128° C.) for 60 minutes and the bath temperature was then increased by 10° C. and kept at this temperature for a total of 8 hours. The reaction was cooled down to below 60° C. and methanol (400 ml) was added. The product (491 g, 1.88 mol, 62% yield) precipitated as a black solid that was isolated by filtration and used directly in the next step without further identification.

Benzofuran-2-acetic acid (4). The thiomorpholide 3 (490 g, 1.88 mol) was dissolved in 12N HCl (1,000 ml) and acetic acid (500 ml). The solution was stirred at reflux temperature for 18 hours. The progress of the reaction was monitored by TLC on silica plates, eluting with methanol/dichloromethane (5:95 v/v). The solvent was evaporated. The product was stirred with cold 1N HCl and filtered with suction and the filtration cake was washed several times with 100-ml portions of 1N HCl, and air-dried for 2 hours. The crude acid was dried at 40° C. in a vacuum oven overnight until constant weight. The crude product weighed 308 g (1.74 mol, 93% yield). An analytical sample was purified on silica ($CH_2Cl_2$/MeOH 5:95) to give a white solid melting at 98.5–99.5° C. Anal. ($C_{10}H_8O_3$) C, H: calculated 68.18, 4.58; found 68.16, 4.57.

Methyl benzofuran-2-acetate (5). Benzofurane-2-acetic acid 4 (305 g, 1.73 mol) was dissolved in methanol (1,000 ml) and concentrated sulfuric acid (20 ml). The mixture, which was originally a suspension, was stirred at reflux for 120 minutes. Half of the methanol was distilled off and a mixture consisting of water, KOH, and ethyl acetate (2,000 ml/65 g/1,000 ml) was added. After mixing well, the organic layer was allowed to separate and was isolated. The aqueous phase was extracted once more with ethyl acetate (500 ml) and the combined organic extracts were dried over sodium sulfate, filtered, and evaporated. The crude product was a reddish oil weighing 316 g, which was purified by flash vacuum distillation at 0.1 mm Hg (bp 80–90° C.). The yield of distilled product, a colorless oil, was 288 g (1.51 mol, 86%). Anal. ($C_{11}H_{10}O_3$) C, H: calculated 69.46, 5.30; found 69.49, 5.36.

Methyl 2-[3-(4-methoxybenzoyl)]benzofuraneacetate (6). The distilled ester 5 (278 g, 1.46 mol), para-anisoyl chloride (248.5 g, 1.46 mol), and anhydrous dichloroethane (800 ml) were added to a 3-liter 3-necked flask fitted with an ice-bath, a mechanical stirrer, an addition funnel, and a thermometer. Tin (IV) chloride (380 g, 1.46 mol) was added in several portions and the mixture was stirred at room temperature under nitrogen for 18 hours. Another portion of dichloroethane (1,200 ml) was added and the solution was poured onto ice. The organic phase was separated and washed again with water, then with a 3% sodium bicarbonate solution, and then again with water. The organic solution was then dried over sodium sulfate, filtered, and the solvent was evaporated. The crude product was stirred in hexane for 24 hours to give an off-white solid that was isolated by filtration and dried. The yield was 366 g (1.13 mol, 77%). A sample (1 g) was purified by column chromatography on silica gel and crystallized from ethyl acetate/hexane. The analytical sample had a melting point of 76.8–77.2° C. Anal. ($C_{19}H_{16}O_5$) C, H: calculated 70.35, 4.98; found 70.46, 5.01.

2-[3-(4-Hydroxybenzoyl)]benzofuraneacetic acid (7). Ester 6 (360 g, 1.13 mol), anhydrous acetonitrile (2.5 L), and anhydrous toluene (5 L) were introduced into a 20 L flask fitted with an efficient reflux condenser, a mechanical stirrer, and a nitrogen inlet. To this was added, while stirring, aluminum iodide (1.5 kg, 3.67 mol) in several portions, then tetrabutylammonium iodide (10 g, catalytic amount). The mixture was then stirred at reflux under nitrogen for 3 hours and the reaction was allowed to cool down to room temperature. Water (1,300 ml) was then added slowly, followed by ethyl acetate (2.5 L). The mixture was then pumped through an in-line filter containing celite, the organic phase was separated, dried over sodium sulfate, and evaporated, to give 285 g (0.96 mol, 85%) of a dark solid that showed one major spot on TLC (silica, ethyl acetate/methanol 90:10). Anal. ($C_{17}H_{12}O_5$) C, H: calculated 68.92, 4.08; found 68.93, 4.10.

2-[3-(3,5-Diiodo-4-hydroxybenzoyl)]benzofuraneacetic acid (8). To compound 7 (280 g, 0.96 mol) in water (5 L) was added potassium carbonate (369 g, 2.88 mol) and iodine beads (487 g, 1.92 mol). The mixture was stirred at room temperature overnight and was washed with ethyl acetate (3×1,000 ml). To the aqueous phase was then added another portion of ethyl acetate (2.5 L) and, slowly, 12N HCl, until the pH of the aqueous phase was about 2.0. The organic phase was then isolated and dried over sodium sulfate. Most of the solvent (80%) was evaporated, and the flask was cooled to between 0 and 4° C. and left at that temperature for 4 hours. The product, a tan solid, was isolated by filtration and was washed with minimum amount of cold ethyl acetate until the color was pale yellow. More product could be isolated by evaporating the filtrate to dryness and triturating the dark residue with cold ethyl acetate. The yield was 431 g (0.79 mol, 82%). Mp. 174–176° C. Anal. ($C_{17}H_{10}O_5I_2$)C, H, I: calculated 37.26, 1.84, 46.41; found 37.44, 1.95, 46.28.

(R)-sec-Butyl 2-[3-(3,5-diiodo-4-hydroxybenzoyl)]benzofuraneacetate (9a). Compound 8 (8.2 g, 15 mmol) was dissolved in (R)-2-butanol (50 ml). Sulfuric acid (0.5 ml) was added, and the mixture was stirred at reflux for 2 hours. The solvent was evaporated and the residue was partitioned between ethyl acetate (50 ml) and 10% sodium bicarbonate solution (100 ml). The organic phase was dried over sodium sulfate. The yield was 7.76 g (13.8 mmol, 92%) of a thick oil. The product was purified by chromatography on silica ($CH_2Cl_2$/MeOH 98:2). Anal. ($C_{21}H_{18}O_5$) C, H, I: calculated 41.75, 3.00, 42.01; found 41.71, 3.02, 41.96.

(S)-sec-Butyl 2-[3-(3,5-diiodo-4-hydroxybenzoyl)]benzofuraneacetate (9b). Compound 8 (8.2 g, 15 mmol) was dissolved in (S)-2-butanol (50 ml). Sulfuric acid (0.5 ml) was added, and the mixture was stirred at reflux for 2 hours. The solvent was evaporated and the residue was partitioned between ethyl acetate (50 ml) and 10% sodium bicarbonate solution (100 ml). The organic phase was dried over sodium sulfate. The yield was 7.76 g (13.8 mmol, 92%) of a thick oil. The product was purified by chromatography on silica ($CH_2Cl_2$/MeOH 98:2). Anal. ($C_{21}H_{18}O_5I_2$) C, H, I: calculated 41.75, 3.00, 42.01; found 41.77, 3.05, 41.89.

(R)-(3-Methyl)-2-butyl 2-[3-(3,5-diiodo-4-hydroxybenzoyl)]benzofuraneacetate (9c). Compound 8 (8.2 g, 15 mmol) was dissolved in (R)-3-methyl-2-butanol (50 ml). Sulfuric acid (0.5 ml) was added, and the mixture was stirred at reflux for 2 hours. The solvent was evaporated and the residue was partitioned between ethyl acetate (50 ml) and 10% sodium bicarbonate solution (100 ml). The organic phase was dried over sodium sulfate. The yield was 7.76 g (13.8 mmol, 92%) of a thick oil. The product was purified by chromatography on silica ($CH_2Cl_2$/MeOH 98:2). Anal. ($C_{22}H_{20}O_5I_2$) C, H, I: calculated 42.74, 3.26, 41.06; found 42.68, 3.21, 40.97.

(S)-(3-Methyl)-2-butyl 2-[3-(3,5-diiodo-4-hydroxybenzoyl)]benzofuraneacetate (9d). Compound 8 (8.2 g, 15 mmol) was dissolved in (S)-3-methyl-2-butanol (50 ml). Sulfuric acid (0.5 ml) was added, and the mixture was stirred at reflux for 2 hours. The solvent was evaporated and the residue was partitioned between ethyl acetate (50 ml) and 10% sodium bicarbonate solution (100 ml). The organic phase was dried over sodium sulfate. The yield was 7.76 g (13.8 mmol, 92%) of a thick oil. The product was purified by chromatography on silica ($CH_2Cl_2$/MeOH 98:2). Anal. ($C_{22}H_2O_5I_2$) C, H, I: calculated 42.74, 3.26, 41.06; found 42.64, 3.29, 41.17.

(R)-sec-Butyl 2-[3-(3,5-diiodo-4-(2-diethylaminoethyloxy)benzoyl)]benzofuraneacetate (10a). Compound 9a (6.9 g, 12.3 mmol) was dissolved in $CH_2Cl_2$ (50 ml) and was added to a solution of diethylaminoethyl chloride, hydrochloride (2.55 g, 14.8 mmol) and benzyltriethylammonium chloride (0.28 g, 1.23 mmol) in water (50 ml). The biphasic medium was stirred vigorously and a 1N NaOH solution (27 ml) was added slowly. After stirring for another 4 hours, the organic phase was isolated and dried over sodium sulfate. The product was purified on silica ($CH_2Cl_2$/MeOH 98:2 then 98:4). The yield was 6.43 g (9.72 mmol, 79%) of a thick greenish oil. Anal. ($C_{27}H_{31}I_2NO_5$) C, H, N, I: calculated 46.11, 4.44, 1.99, 36.09; found 46.13, 4.42, 2.00, 36.12.

(S)-sec-Butyl 2-[3-(3,5-diiodo-4-(2-diethylaminoethyloxy)benzoyl)]benzofuraneacetate (10b). Compound 9b (6.9 g, 12.3 mmol) was dissolved in $CH_2Cl_2$ (50 ml) and was added to a solution of diethylaminoethyl chloride, hydrochloride (2.55 g, 14.8 mmol) and benzyltriethylammonium chloride (0.28 g, 1.23 mmol) in water (50 ml). The biphasic medium was stirred vigorously and a 1N NaOH solution (27 ml) was added slowly. After stirring for another 4 hours, the organic phase was isolated and dried over sodium sulfate. The product was purified on silica ($CH_2Cl_2$/MeOH 98:2 then 98:4). The yield was 6.43 g (9.72 mmol, 79%) of a thick greenish oil. Anal. ($C_{27}H_{31}I_2NO_5$) C, H, N, I: calculated 46.11, 4.44, 1.99, 36.09; found 46.18, 4.46, 2.05, 36.19.

(R)-(3-Methyl)-2butyl2-[3-(3,5-diiodo-4-(2-diethylaminoethyloxy)benzoyl)]benzofuraneacetate (10c). Compound 9c (6.9 g, 12.3 mmol) was dissolved in $CH_2Cl_2$ (50 ml) and was added to a solution of diethylaminoethyl chloride, hydrochloride (2.55 g, 14.8 mmol) and benzyltriethylammonium chloride (0.28 g, 1.23 mmol) in water (50 ml). The biphasic medium was stirred vigorously and a 1N NaOH solution (27 ml) was added slowly. After stirring for another 4 hours, the organic phase was isolated and dried over sodium sulfate. The product was purified on silica ($CH_2Cl_2$/MeOH 98:2 then 98:4). The yield was 6.43 g (9.72 mmol, 79%) of a thick greenish oil. Anal. ($C_2,H_{33}I_2NO_5$) C, H, N, I: calculated 46.88, 4.64, 1.95, 35.38; found 46.91, 4.66, 1.91, 35.49.

(S)-(3-Methyl)-2butyl2-[3-(3,5-diiodo-4-(2-diethylaminoethyloxy)benzoyl)]benzofuraneacetate (10d). Compound 9d (6.9 g, 12.3 mmol) was dissolved in $CH_2Cl_2$ (50 ml) and was added to a solution of diethylaminoethyl chloride, hydrochloride (2.55 g, 14.8 mmol) and benzyltriethylammonium chloride (0.28 g, 1.23 mmol) in water (50 ml). The biphasic medium was stirred vigorously and a 1N NaOH solution (27 ml) was added slowly. After stirring for another 4 hours, the organic phase was isolated and dried over sodium sulfate. The product was purified on silica ($CH_2Cl_2$/MeOH 98:2 then 98:4). The yield was 6.43 g (9.72 mmol, 79%) of a thick greenish oil. Anal. ($C_{28}H_{33}I_2NO_5$) C, H, N, I: calculated 46.88, 4.64, 1.95, 35.38; found 46.93, 4.62, 1.89, 35.54.

Figure 13A:
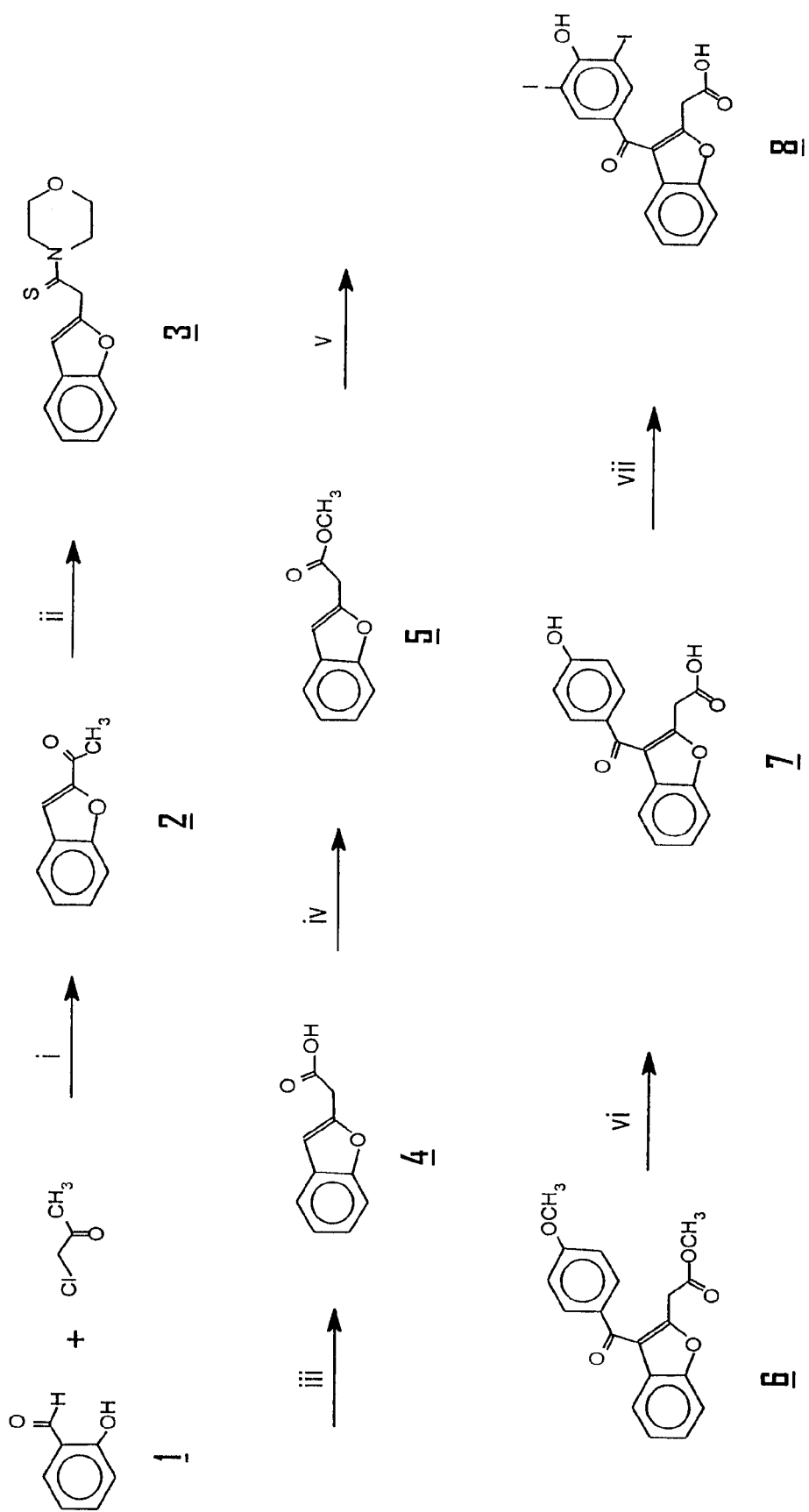
FIGS. 13A–B illustrates the synthesis pathways for R-2042 (10a), S-2042 (10b), R-2055 (10c) and S-2055 (10d).
Figure 13B:
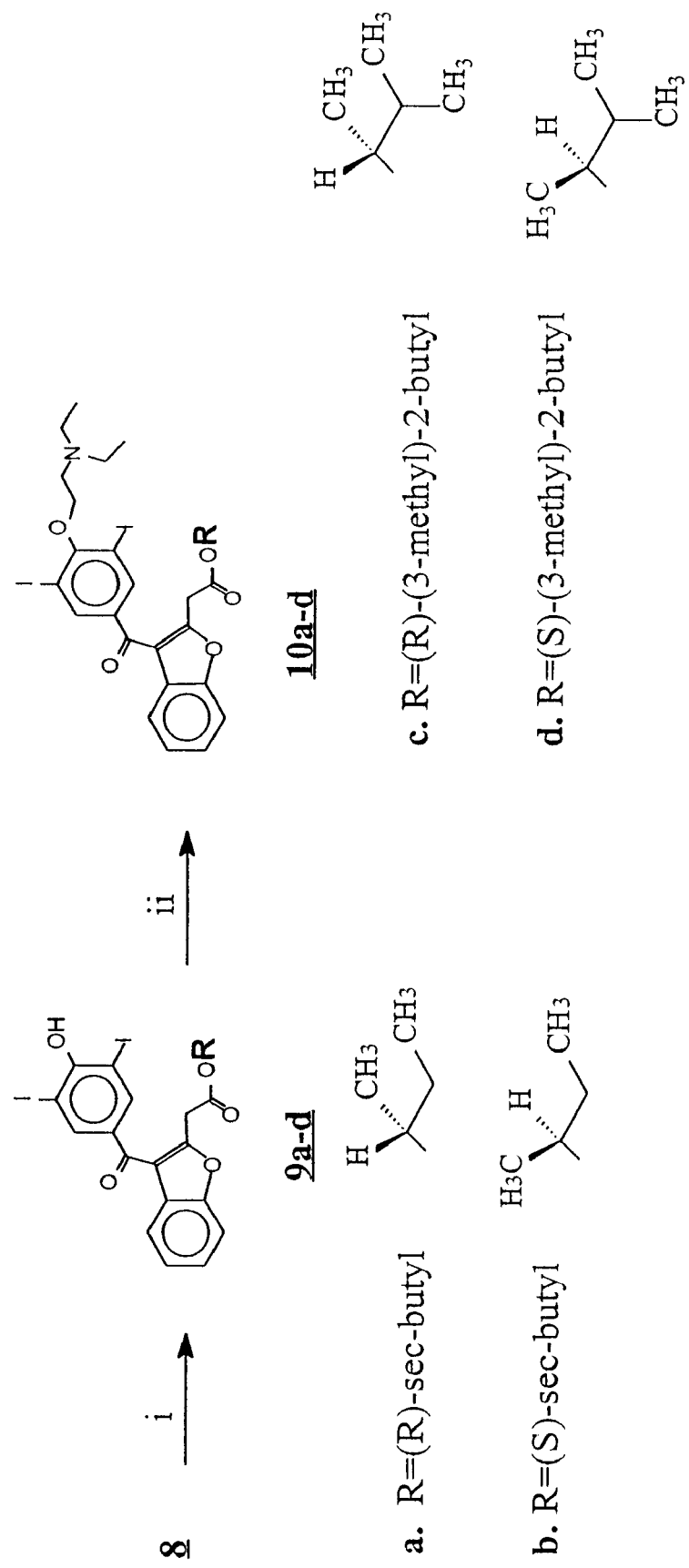
Figure 14:
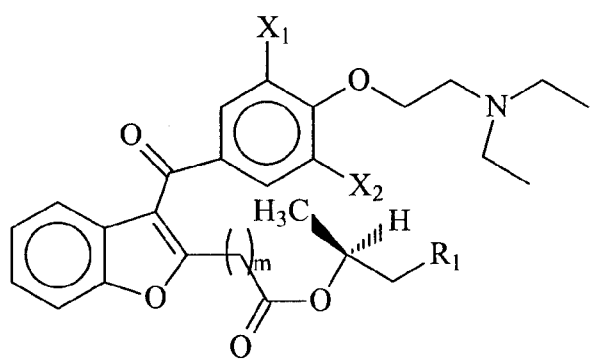
FIG. 14 shows a generic structure covering compound S-2042.
Figure 15:
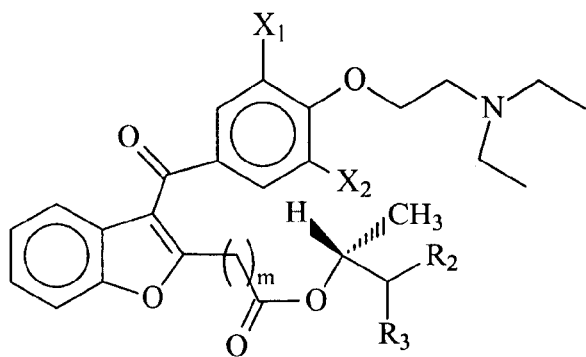
FIG. 15 shows a generic structure covering compound R-2055.
Figure 16:
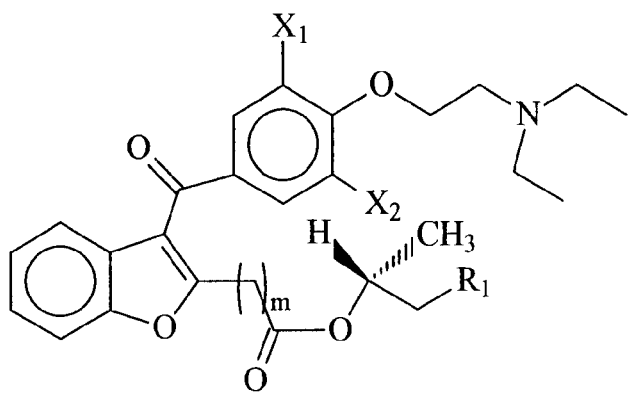
FIG. 16 shows a generic structure covering compound R-2042.
Figure 17:
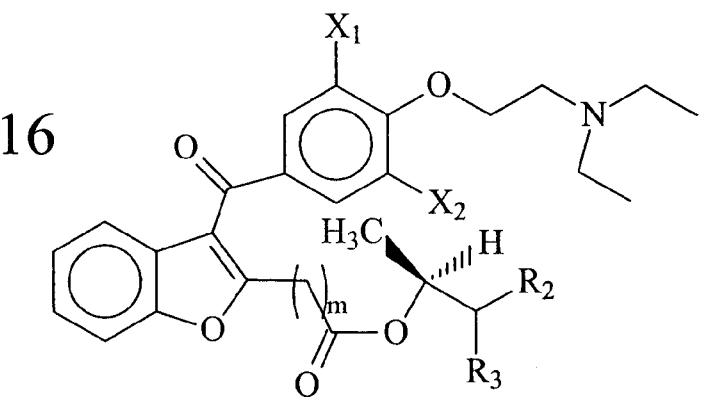
FIG. 17 shows a generic structure covering compound S-2055.
Figure 18:
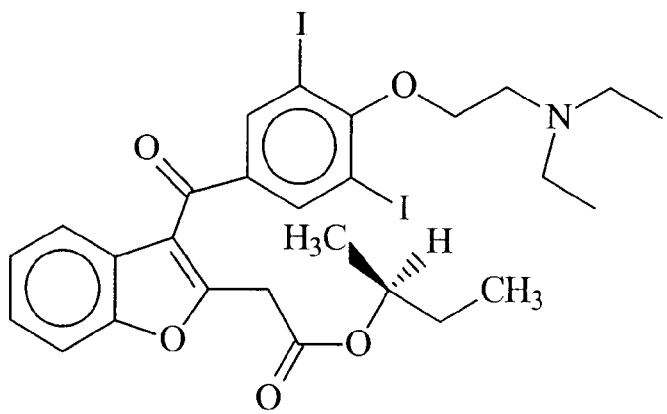
FIG. 18 shows the structure of S-2042.
Figure 19:
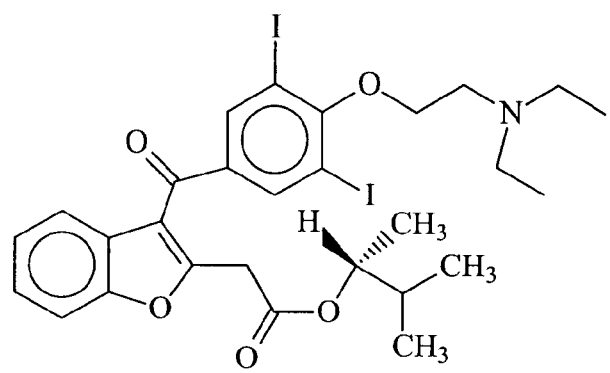
FIG. 19 shows the structure of R-2055.
Figure 20:
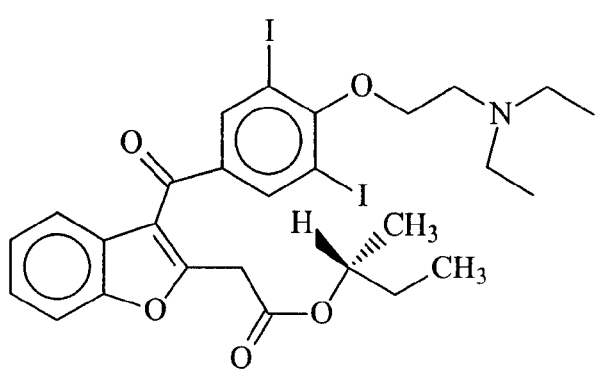
FIG. 20 shows the structure of R-2042.
Figure 21:
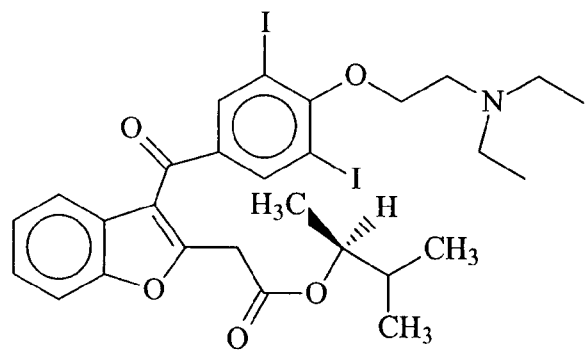
FIG. 21 shows the structure of S-2055.

Formulation as a Sulfate Salt in Water. To compound 10a (3.31 g, 5 mmol.) was added water (200 ml) and 1N sulfuric acid (5.0 ml). The mixture was stirred until a clear solution was obtained. The solution was extracted twice with 50-ml portions of methylene chloride. The extracts were dried over sodium sulfate, filtered, and evaporated in a precisely weighed flask to give a yellow oil. The product was dried under vacuum at room temperature for 2 hours. Water was then added (about 250 ml) to the flask in order to make a 20-mmol/ml solution of 10a, sulfate salt. All the compounds in this series were formulated in a similar way. The pH of the solutions was typically 4.8 to 5.0. Compounds 10b, 10c, and 10d were formulated in a similar manner. An exemplary synthesis pathway is provided in FIGS. 13A–B.

EXAMPLE 8

Novel Synthesis Procedures

One aspect of the subject invention pertains to novel synthetic methods for making esters of benzofuran 2-acetic acid. Example is given for the synthesis of the (S)-2-butyl ester. The synthesis of these esters proceeds via a Wittig type of reaction between 2-coumaranone which is commercially available and an ester of (triphenylphosphoranylidene) acetatic acid, as described below.

A further aspect of this invention pertains to novel synthetic routes for making esters of 3-[4-(2-diethylaminoethoxy)-3,5-diiodobenzoyl]benzofuran 2-acetate. These synthetic routes involve making 4-(2-diethylaminoethoxy)-3,5-diiodobenzoyl chloride, HCl salt,
and coupling 4-(2-diethylaminoethoxy)-3,5-diiodobenzoyl chloride, HCl salt to the ester of benzofurane 2-acetic acid via a Friedel-Crafts type of reaction, using a Lewis acid catalyst (for example tin(IV) chloride) in nitromethane. 4-(2-Diethylaminoethoxy)-3,5-diiodobenzoyl chloride, HCl itself is made by making methyl 3,5-diiodo-4-hydroxybenzoate from 3,5-diiodo-4-hydroxybenzoic acid which is commercially available, then making the 2-diethylaminoethyl ether at the 4-hydroxy position of methyl 3,5-diiodo-4-hydroxybenzoate, then cleaving the methyl ester using aqueous acidic conditions, and finally making the acid chloride using a chlorinating agent such as thionyl chloride. An example of this synthesis is described in detail below.

Previously unknown compounds are made during the course of this synthesis. These compounds are all esters of benzofurane 2-acetic acid (except the methyl ester), 4-(2-diethylaminoethoxy)-3,5-diiodobenzoic acid methyl ester, 4-(2-diethylaminoethoxy)-3,5-diiodobenzoic acid, and 4-(2-diethylaminoethoxy)-3,5-diiodobenzoyl chloride, either as a base or as a HCl salt.

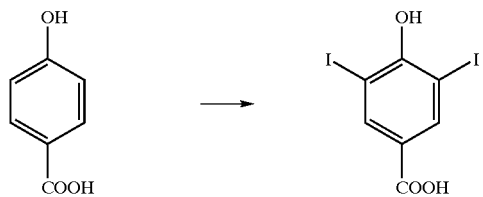

p-Hydroxybenzoic acid (fw: 138.12): 13.8 g, 0.100 mol
Potassium carbonate: 41.5 g, 0.300 mol
Iodine chips: 50.8 g, 0.200 mol
Water: 500 ml Conditions:

Room temperature
4 hours

Workup

Acidify to pH 3.0
Filter
Dissolve in hot acetone (300 ml)
Filter
Evaporate to dryness
Yield: 37.65 g, 0.097 mol (97%) of white solid

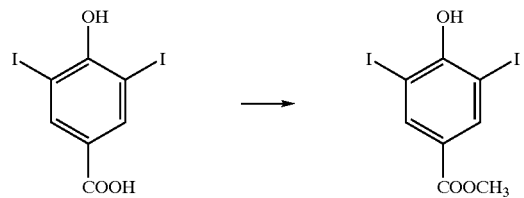

3,5-Diiodo-4-hydroxybenzoic acid (fw:389.9): 37.7 g, 0.097 mol
Thionyl chloride: 25 g
Methanol: 250 ml Conditions:

Reflux temperature
2 hours

Workup:

Leave at room temperature overnight
Filter
Wash with small amount of methanol (10 ml)
Yield: 32.2 g, 0.080 mol (82%) of white solid

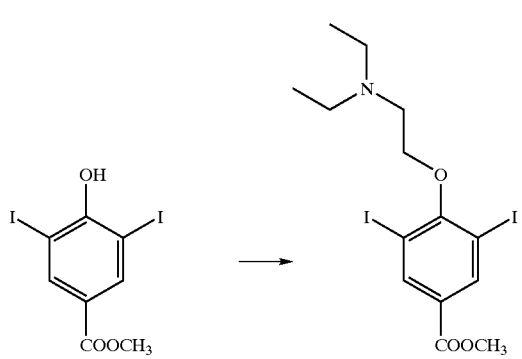

Methyl 3,5-diiodo-4-hydroxybenzoate (fw:403.94): 32.6 g, 0.080 mol
Benzyltriethylammonium chloride: 1.99 g, 0.008 mol
N,N-diethylaminoethylchloride, hydrochloride: 118.79 g, 0.109 mol
Potassium carbonate: 22.4 g, 0.162 mol
Water: 150 ml
Methylene chloride: 150 ml Conditions:

Vigorous stirring at room temperature
4.5 hours

Workup:

Keep organic phase
Dry over magnesium sulfate
Filter
Evaporate
Yield: 37.92 g, 0.075 mol (93%) of colorless oil

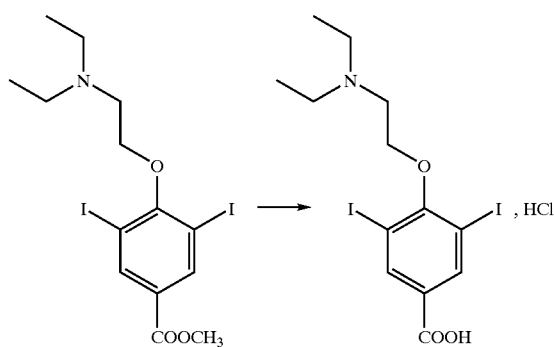

Methyl 4-(2-diethylaminoethoxy)-3,5-diiodobenzoate (fw: 503.12): 37.85 g, 0.075mol
6N HCl Conditions:

Mix well and leave at slow reflux (no stirring) overnight

Workup:

Filter hot
Dry
Yield: 39.3 g, 0.075 mol (quantitative) of white solid

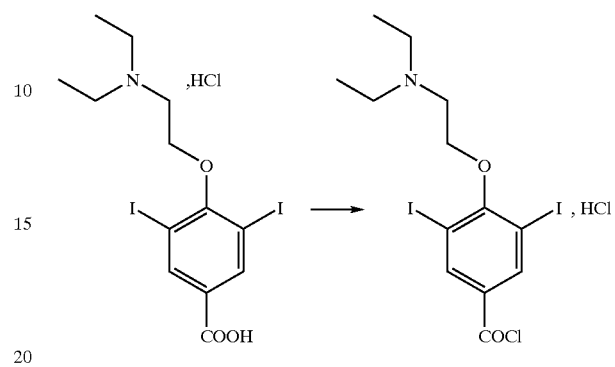

4-(2-Diethylaminoethoxy)-3,5-diiodobenzoic acid, HCl salt (fw: 524.8): 1.56 g, 0.003 mol
Thionyl chloride: 5 ml
DMF: 0.1 ml Conditions:

Add thionyl chloride to ice-cooled material, then add DMF
Transfer to a 50° C. bath
Stir for 3 hours Workup:

Evaporate thionyl chloride
Stir in hot methylene chloride/cyclohexane (30:70) (10 ml)
Cool down
Filter under nitrogen
Yield: 1.59 g, 0.0029 mol (98%) of pale tan solid.

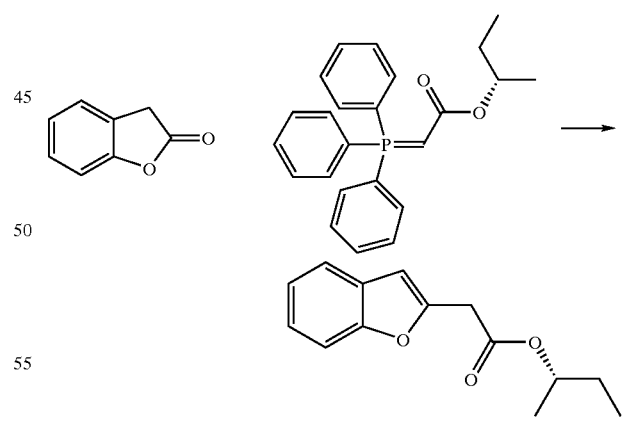

2-Coumaranone: 1.34 g, 0.010 mol
(S)-2-Butyl (triphenylphosphoranylidene)acetate: 3.77 g, 0.010 mol
2-Methoxyethyl ether, anhydrous: 10 ml Conditions:

Stir at between 140 and 162° C. for 12 to 18 hours

Workup:

Cool down to room temperature
Add ethyl acetate (20 ml) and water (20 ml)
Keep ethyl acetate phase
Dry over magnesium sulfate
Filter
Evaporate solvent
Yield: 1.97 g, 0.009 mol (90%)

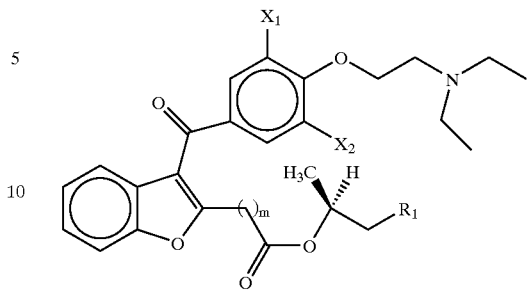

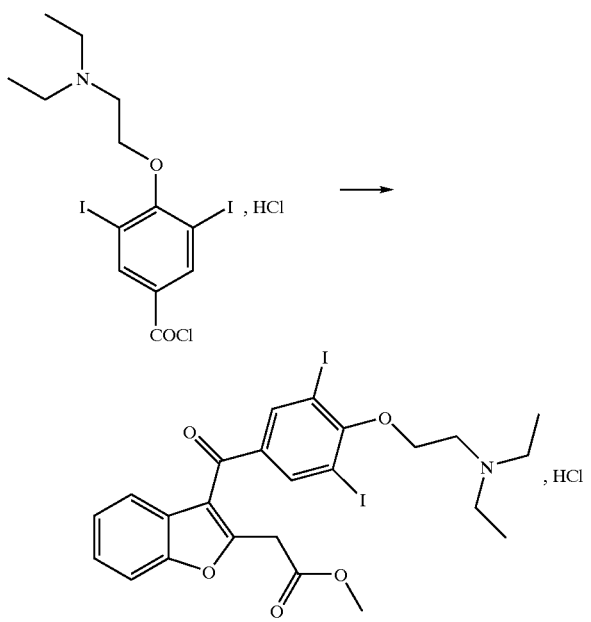

4-(2-Diethylaminoethoxy)-3,5-diiodobenzoyl chloride, HCl salt (fw: 543.3):1.8 g, 0.0033 mol
Methyl benzofuran-2-acetate: 0.5 g, 0.0027 mol
Nitromethane
Tin(IV) chloride: 0.83 g, 0.0032 mol Conditions:

Stir under argon overnight

Workup:

Add 5% sodium bicarbonate solution, stir for 30 min
Add ethyl acetate, keep organic phase
Dry over magnesium sulfate
Evaporate solvent
Yield: 1.39 g, 0.002 mol (74%)

It should be understood that the examples and embodiments described herein are for illustrative purposes only and that various modifications or changes in light thereof will be suggested to persons skilled in the art and are to be included within the spirit and purview of this application.

We claim:

1. A pharmaceutically acceptable salt of a compound having the formula:

(S-2042)

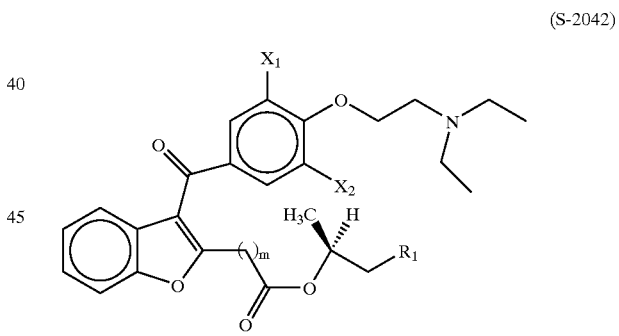

wherein $X_1$ and $X_2$ may be the same or different and are selected from the group consisting of iodine, fluorine, bromine, and chlorine;

m is from 0–10;

$R_1$ is selected from the group consisting of H, $C_{1-20}$ alkyl, $C_{2-20}$ alkenyl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, CN, $NO_2$, and $SO_{2-4}$;

n is one;

wherein said compound is in atleast about 90% enantiomeric excess; and wherein said salt is the salt of an organic acid.

2. The salt, according to claim 1, wherein the salt is the citrate or tartrate salt.

3. A composition comprising a pharmaceutically acceptable salt of a compound having the formula:

(S-2042)

wherein $X_1$ and $X_2$ may be the same or different and are selected from the group consisting of iodine, fluorine, bromine, and chlorine;

m is from 0–10;

$R_1$ is selected from the group consisting of H, $C_{1-20}$ alkyl, $C_{2-20}$ alkenyl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, CN, $NO_2$, and $SO_{2-4}$;

n is one;

wherein said compound is in at least about 90% enantiomeric excess; and wherein said salt is the salt of an organic acid; and wherein said composition further comprises a pharmaceutically acceptable carrier.

4. The composition, according to claim 3, wherein the salt is the citrate or tartrate salt.

5. A method of treating or reducing the incidence of cardiac arrhythmias comprising the administration to an individual of a therapeutically effective amount of a pharmaceutically acceptable salt of a compound having the formula:

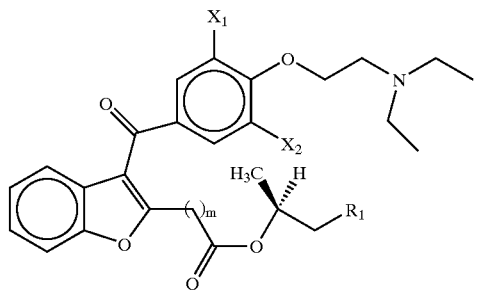

(S-2042)

wherein $X_1$ and $X_2$ may be the same of different and are selected from the group consisting of iodine, fluorine, bromine, and chlorine;

m is from 0–10;

$R_1$ is selected from the group consisting of H, $C_{n-20}$ alkyl, $C_{2-20}$ alkenyl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, CN, $NO_2$, and $SO_{2-4}$;

n is one;

wherein said compound is in at least about 90% enantiomeric excess; and wherein said salt is a salt of an organic acid.

6. The method, according to claim 5, wherein the salt is the citrate or tartrate salt.

7. The method of claim 5, wherein said cardiac arrhythmia is selected from the group consisting of flutter, paroxysmal supraventricular tachycardia, ventricular premature beats, sustained ventricular tachycardia, non-sustained ventricular tachycardia, and ventricular fibrillation.

8. The method of claim 5, wherein said individual is a high risk cardiac patient.

9. The method of claim 8, wherein said patient is a post-myocardial infarction patient.

10. The method of claim 8, wherein said patient has congestive heart failure.

11. A pharmaceutically acceptable salt thereof of a compound having the formula:

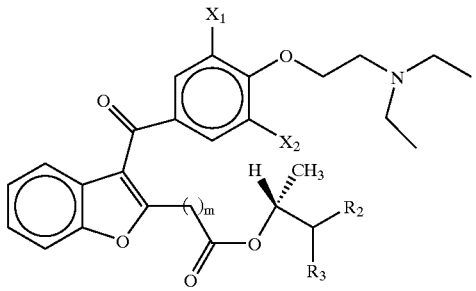

(S-2055)

wherein $X_1$ and $X_2$ may be the same or different and are selected from the group consisting of iodine, fluorine, bromine, and chlorine;

m is from 0–10;

$R_2$ and $R_3$ may be the same or different and are each selected from the group consisting of $C_{2-20}$ alkyl, $C_{2-20}$ alkenyl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, CN, $NO_2$, and $SO_{2-4}$;

n is at least one;

wherein said compound is in at least 90% enantiomeric excess; and wherein said salt is a salt of an organic acid.

12. The salt, according to claim 11, wherein the salt is the citrate or tartrate salt.

13. A composition comprising a pharmaceutically acceptable salt of a compound having the formula:

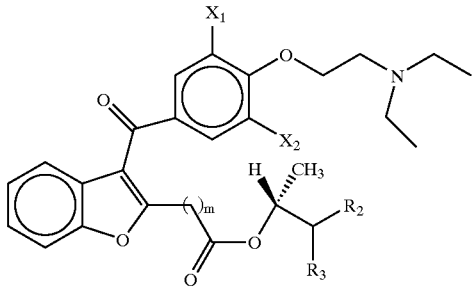

(S-2055)

wherein $X_1$ and $X_2$ may be the same or different and are selected from the group consisting of iodine, fluorine, bromine, and chlorine;

m is from 0–10;

$R_2$ and $R_3$ may be the same or different and are each selected from the group consisting of $C_{n-20}$ alkyl, $C_{2-20}$ alkenyl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, CN, $NO_2$, and $SO_{2-4}$;

n is at least one;

wherein said compound is in at least about 90% enantiomeric excess; and wherein said salt is the salt of an organic acid; and wherein said composition further comprises a pharmaceutically acceptable carrier.

14. The composition, according to claim 3, wherein the salt is the citrate or tartrate salt.

15. A method of treating or reducing the incidence of cardiac arrhythmias comprising the administration to an individual of a therapeutically effective amount of a pharmaceutically salt of a compound having the formula:

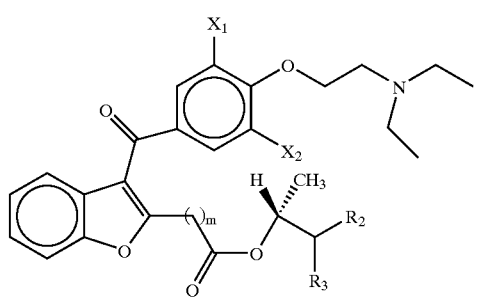

(S-2055)

wherein $X_1$ and $X_2$ may be the same or different and are selected from the group consisting of iodine, fluorine, bromine, and chlorine;

m is from 0–10;

$R_2$ and $R_3$ may be the same or different and are each selected from the group consisting of $C_{n-20}$ alkyl, $C_{2-20}$ alkenyl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, CN, $NO_2$, and $SO_{2-4}$;

n is at least one;

wherein said compound is in at least about 90% enantiomeric excess; and wherein said salt is the salt of an organic acid.

16. The method, according to claim 15, wherein the salt is the citrate or tartrate salt.

17. The method of claim 15, wherein said cardiac arrhythmia is selected from the group consisting of flutter, paroxysmal supraventricular tachycardia, ventricular premature beats, sustained ventricular tachycardia, non-sustained ventricular tachycardia, and ventricular fibrillation.

18. The method of claim 15, wherein said individual is a high risk cardiac patient.

19. The method of claim 18, wherein said patient is a post-myocardial infarction patient.

20. The method of claim 18, wherein said patient has congestive heart failure.

21. A pharmaceutically acceptable salt of a compound having the formula;

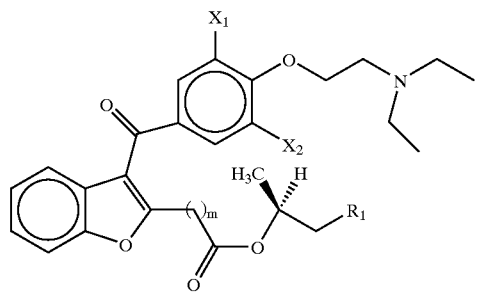

(S-2042)

wherein $X_1$ and $X_2$ may be the same or different and are selected from the group consisting of iodine, fluorine, bromine, and chlorine;

m is from 0–10;

$R_1$ is selected from the group consisting of $C_{n-20}$ alkyl, $C_{2-20}$ alkenyl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, CN, $NO_2$, and $SO_{2-4}$;

n is at least one;

wherein said compound is in at least about 90% enantiomeric excess; and wherein said salt is the salt of an organic acid.

22. The salt, according to claim 21, wherein the salt is the citrate or tartrate salt.

23. A composition comprising a pharmaceutically acceptable salt of a compound having the formula:

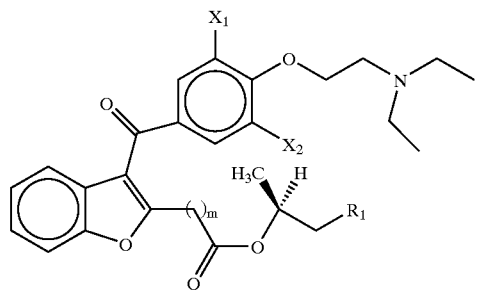

(S-2042)

wherein $X_1$ and $X_2$ may be the same or different and are selected from the group consisting of iodine, fluorine, bromine, and chlorine;

m is from 0–10;

$R_1$ is selected from the group consisting of $C_{n-20}$ alkyl, $C_{2-20}$ alkenyl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, CN, $NO_2$, and $SO_{2-4}$;

n is at least one;

wherein said compound is in at least about 90% enantiomeric excess, and wherein said salt is the salt of an organic acid; and wherein said composition further comprises a pharmaceutically acceptable carrier.

24. The composition, according to claim 3, wherein the salt is the citrate or tartrate salt.

25. A method of treating or reducing the incidence of cardiac arrhythmias comprising the administration to an individual of a therapeutically effective amount of a pharmaceutically acceptable salt of a compound having the formula:

(S-2042)

wherein $X_1$ and $X_2$ may be the same or different and are selected from the group consisting of iodine, fluorine, bromine, and chlorine;

m is from 0–10;

$R_1$ is selected from the group consisting of $C_{n-20}$ alkyl, $C_{2-20}$ alkenyl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be optionally, substituted with a moiety selected from the group consisting of $C_{1-6}$ alkyl, halogen, CN, $NO_2$, and $SO_{2-4}$;

n is at least one;

wherein said compound is in at least about 90% enantiomeric excess, and wherein said salt is the salt of an organic acid.

26. The method, according to claim 25, wherein the salt is the citrate or tartrate salt.

27. The method of claim 25, wherein said cardiac arrhythmia is selected from the group consisting of atrial fibrillation, flutter, paroxysmal supraventricular tachycardia, ventricular premature beats, sustained ventricular tachycardia, non-sustained ventricular tachycardia, and ventricular fibrillation.

28. The method of claim 25, wherein said individual is a high risk cardiac patient.

29. The method of claim 28, wherein said patient is a post-myocardial infarction patient.

30. The method of claim 28, wherein said patient has congestive heart failure.

31. A pharmaceutically acceptable salt thereof of a compound having the formula:

(S-2055)

wherein $X_1$ and $X_2$ may be the same or different and are selected from the group consisting of iodine, fluorine, bromine, and chlorine;

m is from 0–10;

$R_2$ and $R_3$ may be the same or different and are each selected from the group consisting of $C_{n-20}$ alkyl, $C_{2-20}$ alkenyl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, CN, $NO_2$, and $SO_{2-4}$;

n is one;

wherein said compound is in at least about 90% enantiomeric excess; and wherein said salt is the salt of an organic acid.

32. The salt, according to claim 31, wherein the salt is the citrate or tartrate salt.

33. A composition comprising a pharmaceutically acceptable salt of a compound having the formula:

(S-2055)

wherein $X_1$ and $X_2$ may be the same or different and are selected from the group consisting of iodine, fluorine, bromine, and chlorine;

m is from 0–10;

$R_2$ and $R_3$ may be the same or different and are selected from the group consisting of $C_{n-20}$ alkyl, $C_{2-20}$ alkenyl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, CN, $NO_2$, and $SO_{2-4}$;

n is one;

wherein said compound is in at least about 90% enantiomeric excess; and wherein said salt is the salt of an organic acid; and wherein said composition further comprises a pharmaceutically acceptable carrier.

34. The composition, according to claim 3, wherein the salt is the citrate or tartrate salt.

35. A method of treating or reducing the incidence of cardiac arrhythmias comprising the administration to an individual of a therapeutically effective amount of a pharmaceutically acceptable salt of a compound having the formula:

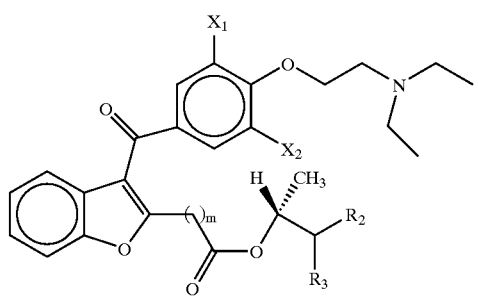

(S-2055)

wherein $X_1$ and $X_2$ may be the same or different and selected from the group consisting of iodine, fluorine, bromine, and chlorine;

m is from 0–10;

$R_2$ and $R_3$ may be the same or different and are selected from the group consisting of $C_{n-20}$ alkyl, $C_{2-20}$ alkenyl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{1-20}$ alkyl-cycloalkyl, any of which may be, optionally, substituted with a moiety selected from the group consisting of $C_{1-6}$ alkyl, halogen, CN, $NO_2$, and $SO_{2-4}$;

n is one;

wherein said compound is in at least about 90% enantiomeric excess; and wherein said salt is the salt of an organic acid.

36. The method, according to claim 35, wherein the salt is the citrate of tartrate salt.

37. The method of claim 35, wherein said cardiac arrhythmia is selected from the group consisting of atrial fibrillation, flutter, paroxysmal supraventricular tachycardia, ventricular premature beats, sustained ventricular tachycardia, non-sustained ventricular tachycardia, and ventricular fibrillation.

38. The method of claim 35, wherein said individual is a high risk cardiac patient.

39. The method of claim 38, wherein said patient is a post-myocardial infarction patient.

40. The method of claim 38, wherein said patient has congestive heart failure.

* * * * *

UNITED STATES PATENT AND TRADEMARK OFFICE
CERTIFICATE OF CORRECTION

PATENT NO. : 6,683,195 B2
DATED : January 27, 2004
INVENTOR(S) : Pascal Druzgala and Peter G. Milner It is certified that error appears in the above-identified patent and that said Letters Patent is hereby corrected as shown below:

Column 1,
Line 10, "No. 09/680,873" should read -- 09/689,873 --.

Column 4,
Line 21, "d, 1-sotalol" should read -- *d, l*-sotalol --.

Column 16,
Line 10, "Anal. ($C_{21}$, $H_{18}O_5$)" should read -- Anal. ($C_{21}H_{18}O_5I_2$) --.
Line 11, "3.00,42.01;" should read -- 3.00, 42.01; --.
Line 46, "Anal. ($C_{22}H_2O_5I_2$)" should read -- Anal. ($C_{22}H_{20}O_5I_2$) --.

Column 17,
Line 20, "Anal. ($C_2H_{33}I_2NO_5$)" should read -- Anal. ($C_{28}H_{33}I_2NO_5$) --.

Column 18,
Line 41, "Workup" should read -- Workup: --.

Column 22,
Lines 21 and 57, "of H, $C_{1-20}$ alkyl" should read -- of H, $C_{n-20}$ alkyl --.
Line 31, "atleast" should read -- at least --.

Column 23,
Line 31, "the same of different" should read -- the same or different --.

Column 24,
Lines 5 and 43, (formula label), "S-2055" should read -- R-2055 --.
Line 25, "consisting of $C_{2-20}$ alkyl" should read -- consisting of $C_{n-20}$ alkyl --.
Line 34, "is in at least 90%" should read -- is in at least about 90% --.

Column 25,
Line 18, (formula label), "S-2055" should read -- R-2055 --.

Column 26,
Line 5, (formula label), "S-2042" should read -- R-2042 --.

Line 5, " [structure] " should read -- [structure] --.

UNITED STATES PATENT AND TRADEMARK OFFICE
CERTIFICATE OF CORRECTION

PATENT NO. : 6,683,195 B2
DATED : January 27, 2004
INVENTOR(S) : Pascal Druzgala and Peter G. Milner It is certified that error appears in the above-identified patent and that said Letters Patent is hereby corrected as shown below:

Column 26 (cont'd),
Line 43, (formula label), "S-2042" should read -- R-2042 --.

Line 43, " 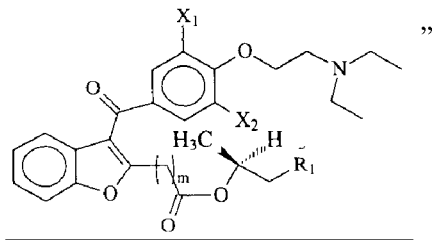 "

should read -- 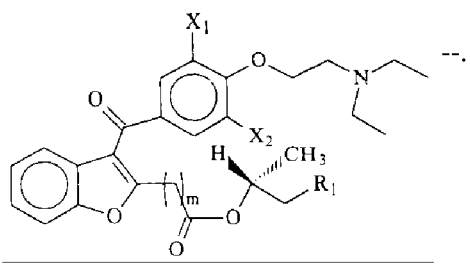 --.

Column 27,
Line 19, "S-2042" should read -- R-2042 --.

Line 19, " 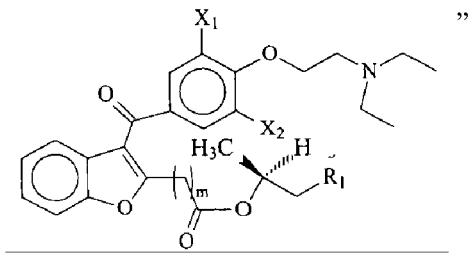 "

should read -- 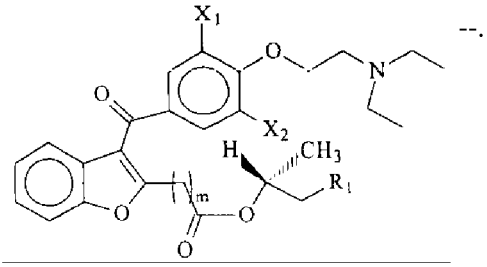 --.

Line 45, "may be optionally", should read -- may be, optionally, --.

UNITED STATES PATENT AND TRADEMARK OFFICE
CERTIFICATE OF CORRECTION

PATENT NO. : 6,683,195 B2
DATED : January 27, 2004
INVENTOR(S) : Pascal Druzgala and Peter G. Milner It is certified that error appears in the above-identified patent and that said Letters Patent is hereby corrected as shown below:

Column 28,
Line 5, " 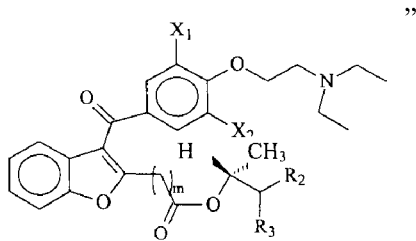 "

should read -- 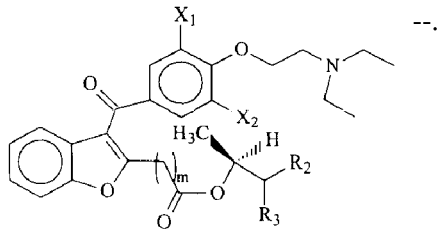 --.

Line 22, "and are each selected" should read -- and are selected --.

Line 40, " 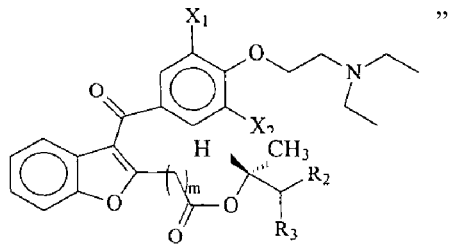 "

should read -- 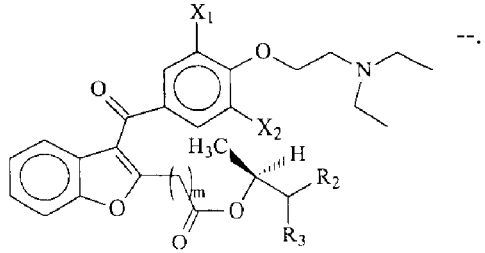 --.

UNITED STATES PATENT AND TRADEMARK OFFICE
CERTIFICATE OF CORRECTION

PATENT NO. : 6,683,195 B2
DATED : January 27, 2004
INVENTOR(S) : Pascal Druzgala and Peter G. Milner It is certified that error appears in the above-identified patent and that said Letters Patent is hereby corrected as shown below:

Column 29,
Line 15, " 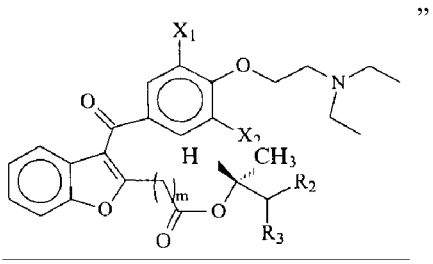 "

should read -- 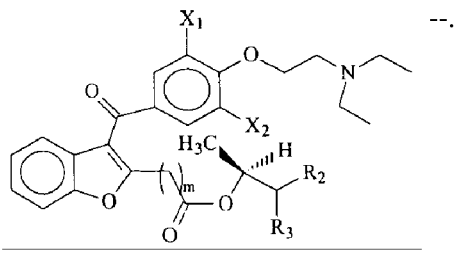 --.

Line 27, "different and selected" should read -- different and are selected --.

Column 30,
Line 16, "the citrate of tartrate salt" should read -- the citrate or tartrate salt --.

Signed and Sealed this

Eighteenth Day of January, 2005

JON W. DUDAS
*Director of the United States Patent and Trademark Office*